US010322118B2

(12) United States Patent
Madden et al.

(10) Patent No.: US 10,322,118 B2
(45) Date of Patent: Jun. 18, 2019

(54) COMPOUNDS AND METHODS FOR INHIBITING CIF VIRULENCE FACTOR

(71) Applicants: Trustees of Dartmouth College, Hanover, NH (US); The Regents of the University of California, Oakland, CA (US)

(72) Inventors: Dean R. Madden, Hanover, NH (US); Christopher D. Bahl, Enfield, NH (US); Bruce D. Hammock, Davis, CA (US); Christophe Morisseau, West Sacramento, CA (US)

(73) Assignees: TRUSTEES OF DARTMOUTH COLLEGE, Hanover, NH (US); THE REGENTS OF TE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/982,298

(22) Filed: Dec. 29, 2015

(65) Prior Publication Data

US 2016/0206605 A1    Jul. 21, 2016

Related U.S. Application Data

(63) Continuation-in-part of application No. 14/386,850, filed as application No. PCT/US2013/035735 on Apr. 9, 2013, now abandoned.

(60) Provisional application No. 61/711,394, filed on Oct. 9, 2012, provisional application No. 61/622,198, filed on Apr. 10, 2012.

(51) Int. Cl.
| | |
|---|---|
| *A61P 11/00* | (2006.01) |
| *A61K 9/00* | (2006.01) |
| *A61K 31/17* | (2006.01) |
| *A61K 31/09* | (2006.01) |
| *A61K 31/445* | (2006.01) |
| *A61K 31/192* | (2006.01) |
| *A61K 31/198* | (2006.01) |
| *A61K 31/085* | (2006.01) |
| *A61K 31/415* | (2006.01) |
| *C12Q 1/34* | (2006.01) |
| *A61K 31/336* | (2006.01) |
| *A61K 31/00* | (2006.01) |

(52) U.S. Cl.
CPC .......... *A61K 31/445* (2013.01); *A61K 9/0073* (2013.01); *A61K 31/00* (2013.01); *A61K 31/085* (2013.01); *A61K 31/09* (2013.01); *A61K 31/17* (2013.01); *A61K 31/192* (2013.01); *A61K 31/198* (2013.01); *A61K 31/336* (2013.01); *A61K 31/415* (2013.01); *A61P 11/00* (2018.01); *C12Q 1/34* (2013.01); *A61K 9/0043* (2013.01); *G01N 2500/02* (2013.01)

(58) Field of Classification Search
CPC .. A61K 31/201; A61K 31/202; A61K 31/336; A61K 9/007; A61K 31/09; A61K 9/0073; A61K 31/17; A61P 11/00
See application file for complete search history.

(56) References Cited

U.S. PATENT DOCUMENTS

| | | | |
|---|---|---|---|
| 2003/0119900 A1 | 6/2003 | Kroetz et al. | 514/475 |
| 2006/0178347 A1 | 8/2006 | Hammock et al. | 514/165 |
| 2007/0116729 A1 | 5/2007 | Palepu | 424/400 |
| 2010/0197593 A1 | 8/2010 | Stanton et al. | 514/6.9 |
| 2010/0317733 A1 | 12/2010 | Hammock et al. | 514/475 |

FOREIGN PATENT DOCUMENTS

| | | | | |
|---|---|---|---|---|
| WO | WO 2006055965 A2 * | 5/2006 | | C07C 59/42 |
| WO | WO-2010066912 A2 * | 6/2010 | | C07C 233/25 |
| WO | WO 2013155047 A2 * | 10/2013 | | G01N 33/6893 |

OTHER PUBLICATIONS

Arand et al. "The Telltale Structures of Epoxide Hydrolase" Drug Metab. Rev. 2003 35:365-383.
Arand et al. "Epoxide Hydrolases: Structure, Function, Mechanism, and Assay" Methods Enzymol. 2005 400:569-588.
Bahl et al. "Crystal Structure of the Cystic Fibrosis Transmembrane Conductance Regulator Inhibitory Factor Cif Reveals Novel Active-Site Features of an Epoxide Hydrolase Virulence Factor" J. Bacteriol. 2010 192:1785-95.
Bahl, C.D. & Madden, D.R. "*Pseudomonas aeruginosa* Cif Defines a Distinct Class of α/β Epoxide Hydrolases Utilizing a His/Tyr Ring Opening Pair" Protein Pept. Lett. 2012 19:186-193.
Bleves et al. "Protein Secretion Systems in *Pseudomonas aeruginosa*: A Wealth of Pathogenic Weapons" Int. J. Med. Microbiol. 2010 300:534-43.
Bomberger et al. "A *Pseudomonas aeruginosa* Toxin that Hijacks the Host Ubiquitin Proteolytic System" PLoS Pathog 2011 7:e1001325.
Davies, J.C. & Bilton, D. "Bugs, Biofilms and Resistance in Cystic Fibrosis" Respir. Care 2009 54:628-40.
Geller, D.E. "Aerosol Antibiotics in Cystic Fibrosis" Respir. Care 2009 54:658-70.
Holmquist, M. "Alpha/Beta-Hydrolase Fold Enzymes: Structures, Functions and Mechanisms" Curr. Protein Pept. Sci. 2000 1:209-235.

(Continued)

*Primary Examiner* — Theodore R. West
(74) *Attorney, Agent, or Firm* — Licata & Tyrrell P.C.

(57) ABSTRACT

The present invention provides a screening assay for identifying inhibitors of *Pseudomonas aeruginosa* CFTR Inhibitory Factor as well as compositions and methods for ameliorating or treating a respiratory disease such as cystic fibrosis or secondary infection thereof.

5 Claims, 1 Drawing Sheet
Specification includes a Sequence Listing.

(56) References Cited

OTHER PUBLICATIONS

MacEachran et al. "The *Pseudomonas aeruginosa* Secreted Protein PA2934 Decreases Apical Membrane Expression of the Cystic Fibrosis Transmembrane Conductance Regulator" Infect. Immun. 2007 75:3902-12.

Martinez-Solano et al. "Chronic *Pseudomonas aeruginosa* Infection in Chronic Obstructive Pulmonary Disease" Clinical Infectious Disease 2008 47:1526-1533.

Morisseau, C. & Hammock, B.D. "Epoxide Hydrolases: Mechanisms, Inhibitor Designs, and Biological Roles" Annu. Rev. Pharmacol. Toxicol. 2005 45:311-333.

Murphy, et al. "*Pseudomonas aeruginosa* in Chronic Obstructive Pulmonary Disease" Am. J. Respir. Crit. Care Med. 2008 177:853-60.

Pinot et al. "Molecular and Biochemical Evidence for the Involvement of the Asp-333-His-523 Pair in the Catalytic Mechanism of Soluble Epoxide Hydrolase" J. Biol. Chem. 1995 270:968-7974.

Rogan et al. "Cystic Fibrosis Transmembrane Conductance Regulator Intracellular Processing, Trafficking, and Opportunities for Mutation-Specific Treatment" *Chest* 2011 139:1480-90.

Salunkhe et al. "A Cystic Fibrosis Epidemic Strain of *Pseudomonas aeruginosa* Displays Enhanced Virulence and Antimicrobial Resistance" J. Bacteriol. 2005 187:4908-20.

Swiatecka-Urban et al. "*Pseudomonas aeruginosa* Inhibits Recycling of CFTR in Polarized Human Airway Epithelial Cells" Am. J. Physiol. Cell Physiol. 2006 290:C862-872.

Ye et al. "Chemotoxicity of Doxorubicin and Surface Expression of P-glycoprotein (MDR1) is Regulated by the *Pseudomonas aeruginosa* Toxin Cif" Am. J. Physiol. Cell Physiol. 2008 295:C807-818.

Zavascki et al. "Reappraisal of *Pseudomonas aeruginosa* Hospital-acquired Pneumonia Mortality in the Era of Metallo-β-lactamase-mediated Multidrug Resistance: A Prospective Observational Study" Crit. Care 2006 10:R114.

International Search Report and Written Opinion in PCT/US2013/035735 dated Oct. 11, 2013.

International Preliminary Report on Patentability in PCT/US2013/035735 dated Oct. 23, 2014.

Baxter et al. "Thyroid hormone mimetics: potential applications in atherosclerosis, obesity and type 2 diabetes" Nature Rev. Drug Discov. 2009 8(4):308-320.

Berkenstam et al. "The thyroid hormone mimetic compound KB2115 lowers plasma LDL cholesterol and stimulates bile acid synthesis without cardiac effects in humans" Proc. Natl. Acad. Sci. USA 2008 105(2):663-667.

Joharapurkar et al. "Selective thyromimetics using receptor and tissue selectivity approaches: prospects for dyslipidemia" J. Med. Chem. 2012 55(12):5649-5675.

* cited by examiner

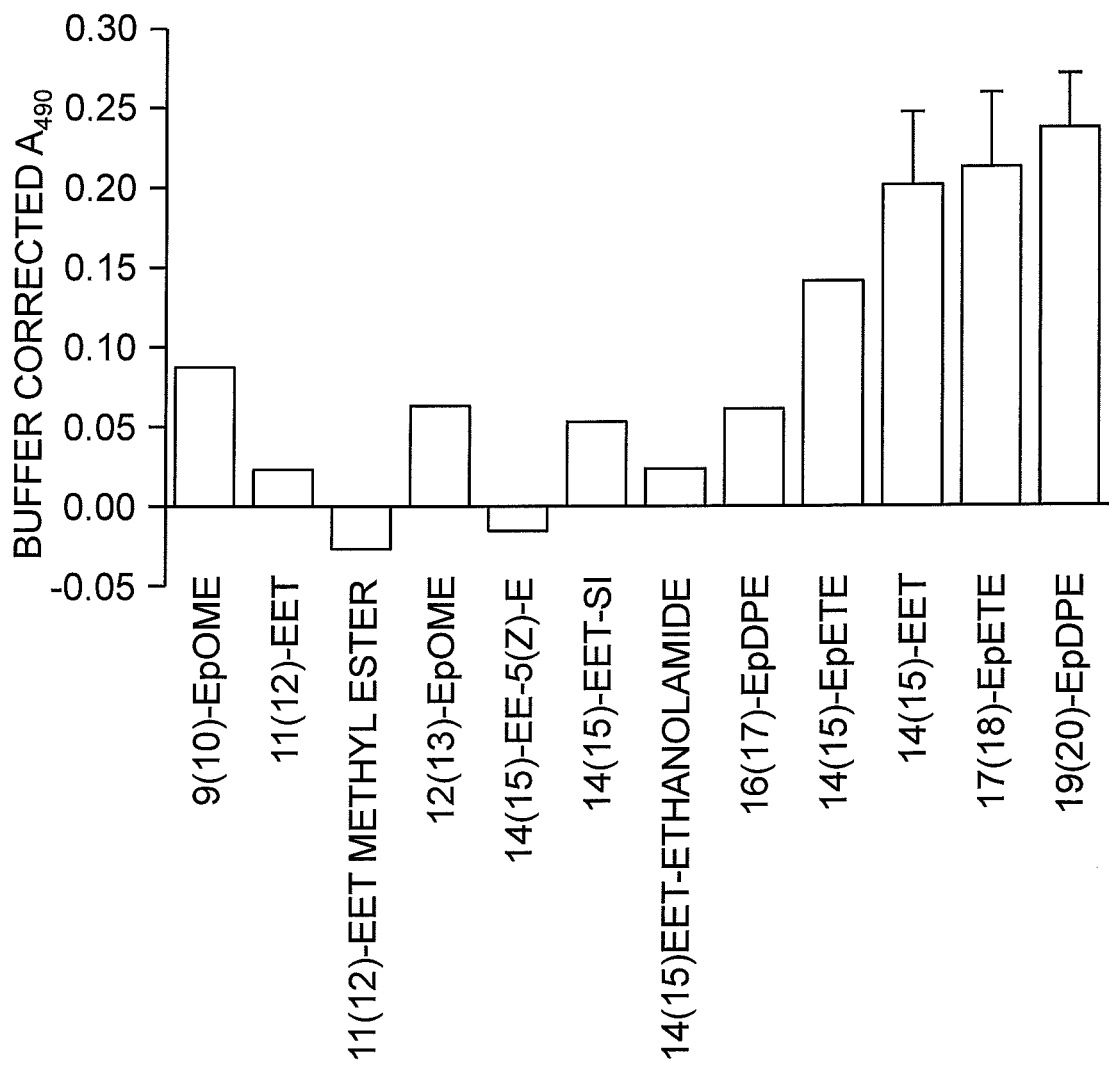

SEQUENCE LISTING

<160> NUMBER OF SEQ ID NOS: 3

<210> SEQ ID NO 1
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 1
tatatcatga caacgcgagg caggccacgg                                    30

<210> SEQ ID NO 2
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 2
ggtagtcatg atgggccct ggaagagcac ctccaggggc caggcgcgca gcgcccgtt    59

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Leu Glu Val Leu Phe Gln Gly Pro
1               5

COMPOUNDS AND METHODS FOR INHIBITING CIF VIRULENCE FACTOR

This application is a continuation-in-part of U.S. application Ser. No. 14/386,850, filed Sep. 22, 2014, which is the U.S. National stage of PCT International Application No. PCT/US2013/035735, filed Apr. 9, 2013, which claims the benefit of priority from U.S. Provisional Patent Application Ser. Nos. 61/622,198, filed Apr. 10, 2012, and 61/711,394, filed Oct. 9, 2012, the contents of each of which are incorporated herein by reference in their entireties.

This invention was made with government support under contract numbers T32-AI007519, T32-DK007301, R01-AI091699, R01-DK075309, R01-E5002710, P42 ES04699, P30-GM106394, T32-GM008704 awarded by the National Institutes of Health. The government has certain rights in the invention. Work on this invention was also supported by grants from the Cystic Fibrosis Foundation.

BACKGROUND OF THE INVENTION

*Pseudomonas aeruginosa* is a Gram-negative opportunistic pathogen that commonly causes ocular and pulmonary infections, as well as burn wound infections. This bacterium possesses an inherent resistance to most antibiotics, and is able to form biofilms that further enhance antibiotic resistance and chronic infections (Davies & Hilton (2009) *Respir. Care* 54:628-40). Of particular clinical importance is the prominence of *P. aeruginosa* infection in patients with compromised pulmonary function. By the age of 18, 80% of all patients with cystic fibrosis (CF) have a chronic *P. aeruginosa* lung infection (Geller (2009) *Respir. Care* 54:658-70). Furthermore, chronic obstructive pulmonary disorder (COPD) is the fourth leading cause of death worldwide (Vogt, et al. (2009) *S D Med.* Spec No 30-7), and *P. aeruginosa* pulmonary infection in these patients results in a rapid decline in lung function and a poor long-term prognosis (Murphy, et al. (2008) *Am. J. Respir. Crit. Care Med.* 177:853-60). *P. aeruginosa* also causes many nosocomial infections, exacerbating ventilator-associated pneumonias and hospital-acquired pneumonia (Zavascki, et al. (2006) *Crit. Care* 10:R114). Recently, a more aggressive strain of *P. aeruginosa* emerged in Liverpool, England that caused an epidemic in the CF community (Salunkhe, et al. (2005) *J. Bacteriol.* 187:4908-20). Therefore, finding new and effective ways to prevent and treat *P. aeruginosa* infection will help to reduce human morbidity and mortality.

During the course of infection, *P. aeruginosa* produces and secretes an arsenal of toxins and virulence factors (Kipnis, et al. (2006) *Med. Mal. Infect.* 36:78-91; Bleves, et al. (2010) *Int. J. Med. Microbiol.* 300:534-43). Of particular interest is the virulence factor Cif (Cystic fibrosis transmembrane conductance regulator Inhibitory Factor), an epoxide hydrolase (EH) that enters human cells and prevents the deubiquitination of the cystic fibrosis transmembrane conductance regulator (CFTR)(Bomberger, et al. (2011) *PLoS Pathog* 7:e1001325). Patients with CF have a mutation in the chloride ion channel CFTR that prevents its function and/or localization to the apical surface of airway epithelial cells, resulting in an osmotic imbalance that dehydrates the airway surface liquid and prevents mucociliary clearance (Rogan, et al. (2011) *Chest* 139:1480-90). Cif induces a rapid decline in cell surface CFTR levels (MacEachran, et al. (2007) *Infect. Immun.* 75:3902-12), essentially phenocopying the genetic disorder CF (Swiatecka-Urban, et al. (2006) *Am. J. Physiol. Cell Physiol.* 290:C862-72). In patients with wild-type CFTR, Cif maintains a persistent infection. In patients with CF that have a *P. aeruginosa* infection, Cif could greatly impede the efficacy of therapies designed to rescue CFTR function. Cif has also been shown to affect other ABC transporters (Ye, et al. (2008) *Am. J. Physiol. Cell Physiol.* 295:C807-818), suggesting that it may have additional deleterious effects on cellular physiology in vivo.

Cif is the first reported example of an epoxide hydrolase utilized as a bacterial virulence factor (Bahl, et al. (2010) *J. Bacteriol.* 192:1785-95). Cif possesses the hallmark catalytic triad that is characteristic of α/β hydrolases, which includes a nucleophile and a charge relay His and acid (Holmquist (2000) *Curr. Protein Pept. Sci.* 1:209-235). Prior to structural elucidation, Cif's catalytic triad His was predicted to be at position 269 by sequence alignment, and this residue was mutated to Ala (MacEachran, et al. (2007) supra). Cif-H269A was found lacking in enzyme activity using the colorigenic EH substrate S-NEPC. This mutant protein was also shown to be deficient in lowering apical surface CFTR abundance of human cells, suggesting a link between EH enzyme activity and the cellular effects of Cif. However, when the structure of Cif was determined by X-ray crystallography, it became clear that His297 was in fact the catalytic triad His (Bahl, et al. (2010) *J. Bacteriol.* 192:1785-1795). The catalytic triad of Cif is buried within the core of the protein at the interface between the cap and core domains. However, His269 is located on the protein surface, and appears to be positioned at the mouth of the tunnel leading to the active site.

To analyze the Cif effect, an understanding of how Cif functions as an EH is needed. EHs are an extensively studied class of enzymes (Arand, et al. (2005) *Methods Enzymol.* 400:569-588; Arand, et al. (2003) *Drug Metab. Rev.* 35:365-383; Morisseau & Hammock (2005) *Annu. Rev. Pharmacol. Toxicol.* 45:311-333). The active site is sequestered within the interior of the protein, at the interface between the α/β hydrolase core domain and a cap domain. According to the canonical mechanism, an epoxide substrate enters the active site and is bound by a ring-opening pair of polar residues. A nucleophile attacks an epoxide carbon, opening the ring and forming a covalent intermediate (Pinot, et al. (1995) *J. Biol. Chem.* 270:968-7974). Further, a charge-relay His-acid pair activates a water molecule to nucleophilically attack the enzyme-substrate intermediate and release the hydrolysis product. While Cif exhibits multiple sequence and structural deviations from the archetypal EH active site (Bahl & Madden (2012) *Protein Pept. Lett.* 19:186-193; Bahl, et al. (2010) supra), their comparison nonetheless allows for a focused analysis.

SUMMARY OF THE INVENTION

The present invention is a pharmaceutical composition formulated for pulmonary administration, which includes an inhibitor of Cif activity in admixture with a pharmaceutically acceptable carrier, wherein the inhibitor is a long chain or very long chain fatty acid monoepoxide or is a compound having the structure of Formula I

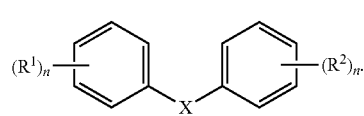

Formula I

In certain embodiments, the pharmaceutical composition is used in a method for ameliorating or treating a respiratory disease (e.g., chronic obstructive pulmonary disease, pneumonia, an *Acinetobacter* infection, a *P. aeruginosa* infection or cystic fibrosis), or a secondary infection thereof (e.g., a viral infection, an *Acinetobacter* or *P. aeruginosa* infection).

Methods for inhibiting the activity of Cif and for identifying an inhibitor of Cif activity are also provided. In accordance with the instant screening assay, a prokaryotic Cif protein is contacted with a test compound in the presence of cyano(6-methoxynaphthalen-2-yl)methyl (oxiran-2-ylmethyl) (CMNGC); and it is determined whether the test compound inhibits hydrolysis of CMNGC.

BRIEF DESCRIPTION OF THE DRAWINGS

FIG. 1 shows the inhibitory activity of fatty acid monoepoxides.

DETAILED DESCRIPTION OF THE INVENTION

*P. aeruginosa* Cif, and Cif proteins from other bacteria, e.g., *Acinetobacter* sp. 13TU RUH2624, are epoxide hydrolases. It has now been found that these bacterial enzymes can be inhibited by tiratricol and a long chain or very long chain fatty acid monoepoxide. In addition to decreasing apical CFTR expression and reducing CFTR-mediated Cl⁻ ion secretion, Cif is able to trigger the degradation of the transporter associated with antigen presentation 1 (TAP-1), which like CFTR is a member of the ABC transporter family. Because of its effect on TAP-1, Cif can impede the immune response to viral infections, which are major contributors to clinical exacerbations in patients with cystic fibrosis. Thus, an inhibitor of Cif enzyme activity is of use in reducing the ability of *P. aeruginosa* to infect patient airways; reducing the ability of *P. aeruginosa* to reverse the effects of CFTR corrector and potentiator compounds in patients with cystic fibrosis (CF); reducing the ability of *P. aeruginosa* to shield viral infections from immune surveillance and reducing infection by a bacterium that expresses a Cif enzyme.

A novel approach was employed to identify Cif inhibitors (iCifs). The assay utilized the fluorogenic reporter compound, cyano(6-methoxynaphthalen-2-yl)methyl (oxiran-2-ylmethyl), which binds the unusual active-site geometry of Cif. Using this reporter compound, together with a weak inhibitor as a positive control, the assay proved robust, and identified a compound, 3,3',5-triiodothyroacetic acid (tiratricol), that potently (4 µM) inhibited Cif enzyme activity. Tiratricol was co-crystallized with the Cif protein, and shown to block the entrance of the tunnel leading to the active site of the enzyme.

Accordingly, the present invention pertains to a screening assay for identifying Cif inhibitors as well as compounds identified by the screening assay for use in compositions and methods for ameliorating or treating a respiratory disease or secondary infection thereof. In accordance with the instant screening assay, Cif protein is contacted with a test compound in the presence of CMNGC and it is determined whether the test compound inhibits hydrolysis of CMNGC, wherein a compound that inhibits hydrolysis of CMNGC is indicative of an inhibitor of Cif activity.

The prokaryotic Cif protein of use in the instant assay can be isolated from its natural source (i.e., *P. aeruginosa* or *Acinetobacter*) or can be produced by recombinant DNA methods or by synthetic chemical methods routinely practiced in the art. For recombinant production, prokaryotic Cif (e.g., *P. aeruginosa*, Accession No. Q9HZR3; *Acinetobacter* sp. 13TU RUH2624, Accession No. D0BWK6) can be expressed in known prokaryotic or eukaryotic expression construct systems. Bacterial, yeast, insect, or mammalian expression systems can be used, as is known in the art.

Alternatively, synthetic chemical methods, such as solid-phase peptide synthesis, can be used to synthesize Cif. General means for the production of proteins are outlined in B. Weinstein, ed., Chemistry and Biochemistry of Amino Acids, Peptides, and Proteins, a Survey of Recent Developments (1983).

Cif can be produced alone or as a fusion protein. A Cif fusion protein includes two protein segments, i.e., Cif fused to another protein segment by means of a peptide bond. The first protein segment includes a full-length Cif protein and can be on the N-terminus or C-terminus of the fusion proteins, as is convenient. The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags (Kodak), influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

Fusion proteins can be made by covalently linking the first and second protein segments or by standard procedures in the art of recombinant DNA technology. Recombinant DNA methods can be used to prepare fusion proteins, for example, by making a DNA construct which includes a nucleic acid sequence encoding Cif in proper reading frame with nucleotides encoding the second protein segment and expressing the DNA construct in a host cell, as is routinely practiced in the art. Many kits for constructing fusion proteins and expressing recombinant proteins are commercially available from companies such as Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada).

Expression of Cif or a Cif fusion protein can be carried out in any suitable host cell including prokaryotic or eukaryotic host cells. A variety of host cells for use in mammalian, yeast, bacterial, or insect expression systems are available and can be used to express the Cif or Cif fusion protein. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, baby hamster kidney cells, HL-60, U937, HaK, or Jurkat cells.

Yeast or prokaryotic host cells can also be used. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus*

*subtilis, Salmonella typhimurium*, or any bacterial strain capable of expressing a recombinant protein.

Expression constructs can be introduced into the host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Once host cells harbor the expression construct encoding the Cif or Cif fusion protein, the host cells are cultured under culture conditions suitable to express the recombinant protein. The resulting expressed protein can then be purified from either the culture medium or the host cells using known techniques.

In accordance with the production of a Cif fusion, such as those of maltose binding protein, glutathione-S-transferase or thioredoxin, the Cif fusion protein can be isolated by affinity chromatography methods. Kits for expression and purification of such fusion proteins are commercially available from New England BioLab (Beverly, Mass.), Pharmacia (Piscataway, N.J.) and Invitrogen. The protein can also be tagged with an epitope and subsequently purified by using a specific antibody directed to the epitope. One such epitope, FLAG, is commercially available from Kodak as are monoclonal antibodies which recognize the FLAG epitope.

The screening method of the present invention can be carried out using any suitable assay format, e.g., multi-well plates, arrays of Cif protein on plates, and the like, that allows rapid preparation and processing of multiple reactions. Stock solutions of the agents as well as assay components are prepared manually and all subsequent pipetting, diluting, mixing, washing, incubating, sample readout and data collecting can be carried out using commercially available robotic pipetting equipment, automated work stations, and analytical instruments for detecting the output of the assay.

In addition to the reagents provided above, a variety of other reagents can be included in the screening assays of the invention. These include reagents like salts, neutral proteins, e.g., albumin, detergents, etc. Also, reagents that otherwise improve the efficiency of the assay, such as protease inhibitors, nuclease inhibitors, and the like can be used.

Test agents that can be screened in accordance with the methods of the present invention are generally derived from libraries of agents or compounds. Such libraries can contain either collections of pure agents or collections of agent mixtures. Examples of pure agents include, but are not limited to, proteins, antibodies, aptamers, peptides, proteinase inhibitors, nucleic acids, oligonucleotides, iRNA, carbohydrates, lipids, synthetic or semi-synthetic small organic molecules, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active agent from the mixture for characterization and development as a therapeutic drug. In particular, the mixture so identified can be sequentially fractionated by methods commonly known to those skilled in the art which can include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained. In particular embodiments, the test compound is a derivative or analog of tiratricol, e.g., as presented by Formula III herein.

As indicated, the screening method involves contacting Cif protein with a test compound in the presence of CMNGC; and determining whether the test compound inhibits hydrolysis of CMNGC by Cif. The step of determining whether hydrolysis of CMNGC by Cif has been inhibited can be carried out as described herein by detecting the fluorescent signal generated upon hydrolysis of CMNGC. In some embodiments, a test compound is selected as a Cif inhibitor if it decreases the fluorescent signal by, e.g., 10%, 20%, 30%, 40%, 50%, 60%, 70%, 80%, 90%, or 95% as compared to a control, e.g., a Cif protein not contacted with an inhibitor. Inhibitors identified by the instant screening assay find application in inhibiting Cif activity as well as in the amelioration or treatment of one or more of the respiratory diseases described herein.

As demonstrated herein, several classes of compounds were shown to inhibit the hydrolysis of CMNGC by Cif. In particular, it has been shown that tiratricol, and derivatives thereof; urea-based scaffolds; and scaffolds based on human signaling epoxide compounds, e.g., derived from long and very long chain fatty acids can inhibit Cif activity. Accordingly, the present invention also features the use of such compounds, either individually or in combination, in compositions for inhibiting the activity of Cif protein and in the treatment of respiratory diseases such as chronic obstructive pulmonary disease, pneumonia and cystic fibrosis or secondary infections thereof.

Compounds within the scope of this invention include those having the structure shown in Formula I.

Formula I

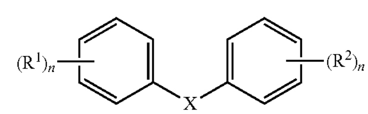

Compounds of Formula I include tiratricol, as well as derivatives and analogs thereof, and urea-based compounds. For the purposes of the present invention, Formula I includes, but is not limited to, diphenyls, diphenylethers, diphenylamines, diphenylmethanes with the substituents of tiratricol, or a diphenyl structure modified to include additional substituents (e.g., O, N, S, OH, $CH_3$, halo groups, phenyl groups, alkyl groups, etc.), remove substituents (e.g., O, N, S, OH, $CH_3$, halo groups, phenyl groups, alkyl groups, etc.), or substitute groups (e.g., substitute one halo group for another) in order to provide compounds with improved activity and/or efficacy.

Tiratricol is known in the art as a thyroid hormone analog of use in the treatment of goiter (Alvarez, et al. (2004) *Horm. Metab. Res.* 36:291-7), as a supplement for weight loss (Devoto & Aravena (2001) *Rev. Med. Chil.* 129:691-3) and for neutralizing bacterial endotoxins (Cascales, et al. (2008) *Chem. Biol. Drug Design* 72:320-28).

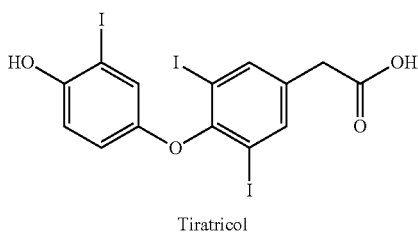 [SMILES: O=C(O)Cc1cc(I)c(Oc2ccc(O)c(I)c2)c(I)c1]

Tiratricol

Tiratricol derivatives have been described. For example, GB 803149 teaches compounds having the structure of Formula II,

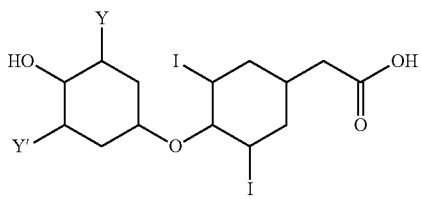

Formula II wherein Y is hydrogen or iodine and Y' is iodine.

Similarly, GB 805761 teaches compounds having the structure of Formula III,

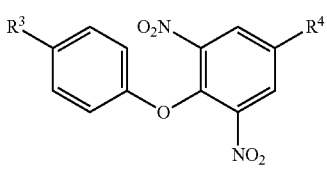

Formula III wherein $R^3$ is a hydroxyl group or a group readily convertible thereto and $R^4$ is a group readily convertible to an acetic acid side chain.

Thus, in accordance with compounds having the structure of Formula I,

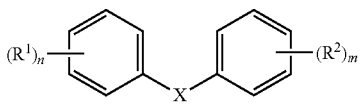

Formula I wherein X is absent (i.e., resulting in a diphenyl) or present and when present is —O—, —NH—, —S—, —CH$_2$—, —NHC(O)NH—, or —C(O)NHC(O)NH—;

n is 0 to 5;
m is 0 to 5; and
$R^1$ and $R^2$ are substituted one or more times anywhere on their respective rings, wherein each occurrence of $R^1$ and $R^2$ is independently a hydrogen, hydroxyl, amino, cyano, halo, nitro, mercapto, phosphate, —SO$_2$NH$_2$, —COOH, —C(O)CH$_3$, —CO$_2$Me, —CONHNH$_2$, —CONHCH$_3$, —NHC(O)R$^{11}$, —OCH$_2$COOH, —OC(O)CH$_2$CH$_3$, alkyl, alkenyl, alkynyl, aryl, alkoxy, or amido group, wherein $R^{11}$ is an alkyl, amino, —(CH$_2$)$_x$C(O)OCH$_2$CH$_3$, or —(CH$_2$)$_x$COOH group, wherein x is 1 to 5.

In certain embodiments, n and m are each independently at least 1, 2 or 3.

In other embodiments, compounds of the invention have the structure of Formula IV,

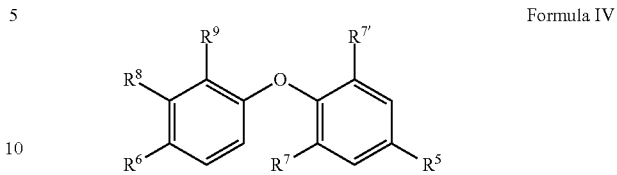

Formula IV wherein $R^5$ is amino, nitro, or —NHC(O)R$^{11}$ group;
$R^6$ is a hydroxyl group;
$R^7$ and $R^{7'}$ are independently a hydrogen or halo group;
$R^8$ is an hydroxyl, amino, cyano, halo, nitro, mercapto, phosphate, —SO$_2$NH$_2$, —COOH, —C(O)CH$_3$, —CO$_2$Me, —CONHNH$_2$, —CONHCH$_3$, —NRC(O)R$^{11}$, —OCH$_2$COOH, —OC(O)CH$_2$CH$_3$, alkyl, alkenyl, alkynyl, aryl, alkoxy, or amido group;
$R^9$ is a hydrogen group;
$R^{11}$ is alkyl, amino, —(CH$_2$)$_x$C(O)OCH$_2$CH$_3$, or —(CH$_2$)$_x$COOH, wherein x is 1 to 5.

As used herein, the term "amino" means —NH$_2$; the term "nitro" means —NO$_2$; the term "halo" designates —F, —Cl, —Br or —I; the term "cyano" means —CN; the term "hydroxyl" means —OH, the term "mercapto" means —SH; the term "phosphate" means —OP(O)(OH)$_2$; and the term "amido" means —C(O)NH$_2$.

The term "alkyl" refers to a radical, having a single saturated carbon atom as the point of attachment, no carbon-carbon double or triple bonds, further having a linear or branched, cyclic or acyclic structure. The term alkyl is intended to include substituted and unsubstituted alkyls. Unless otherwise indicated alkyls of the invention have between 1 and 6 carbon atoms, e.g., methyl, ethyl, propyl, isopropyl, butyl, isobutyl, sec-butyl, tert-butyl, pentyl and hexyl groups.

The term "alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure. The term alkenyl is intended to include substituted and unsubstituted alkenyls. Unless otherwise indicated alkenyls of the invention have between 1 and 6 carbon atoms.

The term "alkynyl" refers to a radical, having a single nonaromatic carbon atom as the point of attachment and at least one nonaromatic carbon-carbon triple bond, further having a linear or branched, cyclic or acyclic structure. The term alkynyl is intended to include substituted and unsubstituted alkynyls. Unless otherwise indicated alkynyls of the invention have between 1 and 6 carbon atoms.

The term "aryl" refers to a radical, having a single carbon atom as point of attachment, wherein the carbon atom is part of an aromatic ring structure containing only carbon atoms. The term aryl is intended to include substituted and unsubstituted aryls. Unless otherwise indicated aryls of the invention have between 5 and 7 carbon atoms.

The term "alkoxy" refers to a radical —OR where R is alkyl as defined herein, e.g., methoxy, ethoxy, propoxy, or 2-propoxy, n-, iso-, or tert-butoxy, and the like.

The term "substituted," when used to modify a class of organic radicals (e.g., alkyl, aryl, etc.), means that one, or more than one, hydrogen atom of that radical has been replaced by a heteroatom, or a heteroatom containing group. Exemplary substituents include, but are not limited to, oxo, hydroxyl, amino, cyano, halo (e.g., trifluoro), nitro, mercapto, phosphate, —COOH, —CO₂Me, CONH₂, —CONHNH₂, or alkyl groups.

The term "unsubstituted," when used to modify a class of organic radicals (e.g., alkyl, aryl, etc.) means that none of the hydrogen atoms of that radical have been replaced with a heteroatom or a heteroatom containing group.

Monoepoxide derivatives of long chain (13 to 21 carbons) and very long (longer than 22 carbons) chain fatty acids are also of use in inhibiting Cif activity. The epoxyeicosatrienoic acids (all with cis configuration) are produced from arachidonic acid by cytochrome P450 epoxygenase (Zhu, et al. (1995) *Hypertension* 25:854). Four isomers are formed: 5,6-, 8,9-, 11,12-, and 14,15-EET.

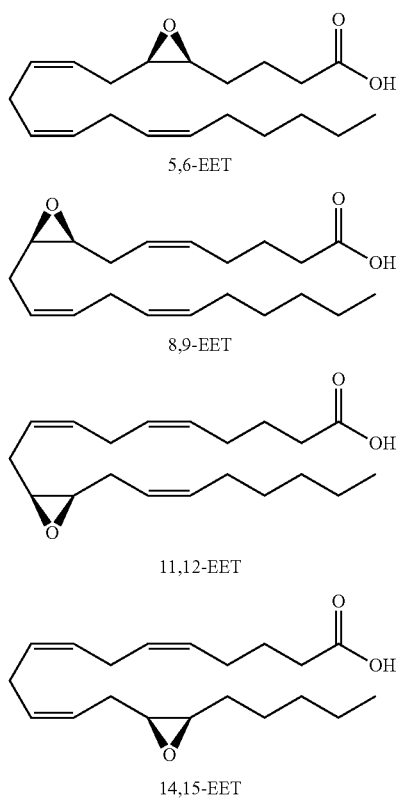

5,6-EET 8,9-EET 11,12-EET 14,15-EET

In addition, Falck, et al. ((2003) *Am. J. Physiol. Heart Circ. Physiol.* 284:H337-H349) disclose 19 analogs of 14,15-EET and a series of 14,15-epoxyeicosatrienoyl-sulfonamides are described by Yang, et al. ((2007) *J. Pharmacol. Exp. Therapeut.* 321:1023-31).

Besides arachidonic acid, epoxide derivatives have been synthesized from EPA (20:5n-3) (Van Rollins (1990) *Lipids* 25:481) and DHA (22:6n-3) (Van Rollins, et al. (1984) *J. Biol. Chem.* 259:5776). These derivatives, epoxyeicosaquatraenoic acid (EpEQE) from EPA and epoxydocosapentaenoic acid (EpDPE) are also generated by the action of renal and hepatic cytochrome P-450 monooxygenases (Fer, et al. (2008) *Arch. Biochem. Biophys.* 471:116). In the rat brain and spinal cord, the regioisomers 17,18-EpEQE and 7,8-EpDPE are the most abundant.

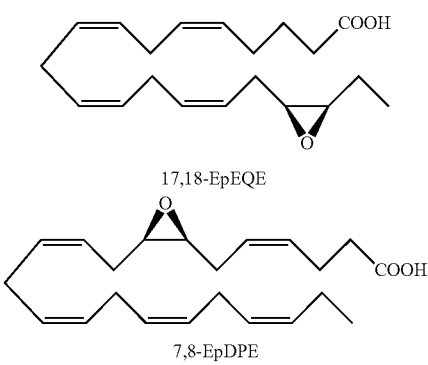

17,18-EpEQE 7,8-EpDPE

Furthermore, 19,20-EpDPE is a docosahexaenoic acid (DHA) epoxygenase metabolite, derived via epoxidation of the omega-3 double bond of DHA and 17,18-epoxyeicosatetraenoic acid (EpETE) is biosynthesized by stereospecific epoxidation of the omega-3 bond of eicosapentaenoic acid (EPA) (Morisseau, et al. (2010) *J. Lipid Res.* 51:3481).

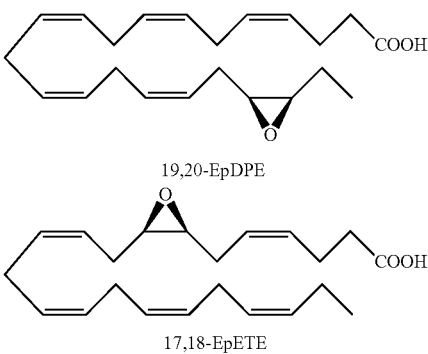

19,20-EpDPE 17,18-EpETE

Other known fatty acid monoepoxides include, but are not limited to, 9,10-epoxyeicosatetraenoic acid (EpOME)); 12,13-EpOME; α 9,10-epoxyoctadecadienoic acid (EpODE); 12,13-EpODE; α 15,16-EpODE; 8,9-EpETE; 11,12-EpETE; 14,15-EpETE; 10,11-EpDPE; 13,14-EpDPE; and 16,17-EpDPE (Morisseau, et al. (2010) supra).

Accordingly, in some embodiments, the inhibitory compound of this invention is a long chain or very long chain fatty acid monoepoxide. In particular embodiments, the inhibitor of the invention is a long chain omega-3 fatty acid (e.g., octadecatrienoic acid (ALA), octadecatetraenoic acid, eicosatrienoic acid (ETE), eicosatetraenoic acid (ETA), eicosapentaenoic acid (EPA) or heneicosapentaenoic acid (HPA)); epoxide derivative of a very long chain omega-3 fatty acid (e.g., docosapentaenoic acid (DPA) or docosahexaenoic acid); epoxide derivative of a long chain omega-6 fatty acid (e.g., octadecadienoic acid, eicosadienoic acid, dihomo-gamma-linolenic acid (DLGA) or arachidonic acid (AA)); or epoxide derivative of a very long chain omega-6 fatty acid (e.g., docosadienoic acid, adrenic acid, or docosapentaenoic acid). In particular embodiments, the fatty acid epoxide of the invention is an EET, EpETE or EpDPE. In yet other embodiments, the long chain or very long chain fatty acid monoepoxide is all-cis, all-trans or a mixture and cis and trans fatty acid.

Long or very long chain fatty acid epoxides of this invention can be naturally occurring, synthetically produced or enzymatically produced using an epoxygenase. In addition, the fatty acid epoxides of this invention include methyl esters, ethanolamides, sulfonamides and sulfonimides.

As with the initial screens, the activity of fatty acid epoxides and compounds within the scope of Formula I and can be screened via the assay described herein.

Compounds Formula I or fatty acid epoxides, as well as compounds disclosed in Tables 8 and 14-18, are Cif inhibitors, which are of use in a method for blocking or inhibiting the activity of Cif. Such a method involves contacting a Cif protein either in vitro or in vivo with an effective amount of a Cif inhibitor so that the activity of the Cif is inhibited or reduced. An effective amount of an inhibitor is an amount that reduces the activity of the Cif by 10%, 20%, 30%, 40%, 50%, 60%, 70%, 80%, 90% or 100%. Such activity can be monitored by enzymatic assays detecting activity of the Cif or by monitoring proteins regulated by Cif (e.g., CFTR or TAP-1).

As indicated, the inhibition of Cif is of use in reducing the ability of *P. aeruginosa* to infect patient airways; reducing the ability of *P. aeruginosa* to reverse the effects of CFTR corrector and potentiator compounds in patients with cystic fibrosis; and reducing the ability of *P. aeruginosa* to shield viral infections from immune surveillance. In addition, *P. aeruginosa* is also a common pathogen in patients suffering from burns. Therefore, a Cif inhibitor could be useful in burn treatment. Moreover, it has been shown that the Cif from *Acinetobacter* sp. 13TU RUH2624 can be inhibited by tiratricol. Accordingly, the present invention also features a method for ameliorating or treating a respiratory disease, or a secondary infection thereof, by administering to a subject in need of treatment a pharmaceutical composition containing a compound of Formula I or fatty acid epoxides, or a compound disclosed in Table 8 or 14-18. In most cases the subject being treated will be a human being, but treatment of agricultural animals, e.g., livestock and poultry, and companion animals, e.g., dogs, cats and horses, is also contemplated. The dosage or effective amount of the Cif inhibitor is an amount which achieves the desired outcome of ameliorating or reducing at least one sign or symptom of a respiratory disease, or a secondary infection thereof.

In particular embodiments of this invention, the respiratory disease being ameliorated or treated is chronic obstructive pulmonary disease, pneumonia, a *P. aeruginosa* infection, an *Acinetobacter* infection or cystic fibrosis. As described herein, subjects with CF, COPD or pneumonia exhibit an exacerbation of their respiratory disease when the lungs of said subjects become infected with *P. aeruginosa*. As such, inhibition of Cif activity in these subjects will result in the amelioration or treatment of the respiratory disease. Furthermore, given its effect on TAP-1, Cif can impede the immune response to viral infections, which are major contributors to clinical exacerbations in patients with cystic fibrosis. Therefore, in other embodiments of the present invention, the Cif inhibitor ameliorates or treats a secondary infection of a subject with a respiratory disease, wherein the secondary infection includes, but is not limited to a viral infection, an *Acinetobacter* infection or a *P. aeruginosa* infection.

To evaluate the efficacy of compounds of the invention, one of skill will appreciate that a model system of, e.g., CF with a *P. aeruginosa* infection, can be utilized to evaluate the adsorption, distribution, metabolism and excretion of a compound as well as its potential toxicity in acute, sub-chronic and chronic studies.

For therapeutic use, it is desirable that the compounds of the present invention are provided to a subject in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, is typically a liquid or solid filler, diluent, excipient, or solvent encapsulating material. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In some embodiments, the pharmaceutical composition is appropriately formulated for systemic administration. In other embodiments, the pharmaceutical composition is appropriately formulated for pulmonary administration. For the purposes of the present invention, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli, and the like).

Pulmonary delivery can be achieved by different approaches, including the use of nebulized, aerosolized, micellular and dry powder-based formulations; administration by inhalation may be oral and/or nasal. Delivery can be achieved with liquid nebulizers, aerosol-based inhalers, and dry powder dispersion devices. One of the benefits of using an atomizer or inhaler is that the potential for contamination is minimized because the devices are self-contained. Dry powder dispersion devices, for example, deliver drugs that may be readily formulated as dry powders. A Cif inhibitor composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

Examples of pharmaceutical devices for aerosol delivery include metered dose inhalers (MDIs), dry powder inhalers (DPIs), and air-jet nebulizers. Exemplary delivery systems by inhalation which can be readily adapted for delivery of the instant compound are described in, for example, U.S. Pat. Nos. 5,756,353; 5,858,784; WO 98/31346; WO 98/10796; WO 00/27359; WO 01/54664; and WO 02/060412. Other aerosol formulations that may be used for delivering the instant compounds are described in U.S. Pat. Nos. 6,294,153; 6,344,194; 6,071,497; WO 02/066078; WO 02/053190; WO 01/60420; and WO 00/66206.

The invention is described in greater detail by the following non-limiting examples.

Example 1: Cif Epoxide Hydrolase Enzyme Activity is Required for CFTR Inhibitory Activity Mutagenesis and Protein Purification.

D129S, E153D, and E153Q mutations were generated using an in vivo yeast recombineering technique as previously described (MacEachran, et al. (2007) supra; Shanks, et al. (2006) Appl. Environ. Microbiol. 72:5027-5036). The H177A, Y239F and H207A mutations were generated by altering the coding sequence of the wild-type Cif expression plasmid pDPM73 (MacEachran, et al. (2007) supra) using the QUIKCHANGE Lightning Site-Directed Mutagenesis Kit (Stratagene). Carboxy-terminal hexa-histidine-tagged Cif protein was expressed in TOP10 Escherichia coli (Invitrogen) cells and purified by immobilized metal affinity chromatography according to established methods (Bahl, et al. (2010) Acta Crystallogr. F66:26-28). Purified Cif protein was prepared in the following buffer: 100 mM NaCl, 20 mM sodium phosphate (pH 7.4).

Crystallization, Data Collection and Processing, Structure Refinement, and Analysis.

Cif protein crystals were obtained by vapor diffusion against 400 μl of reservoir solution in a 4 μl hanging drop at 291 K (Bahl, et al. (2010) supra). Drops were set up by mixing the reservoir solution with Cif protein in a 1:1 ratio. Crystallization reservoir solutions are provided in Table 1.

TABLE 1

| Mutant | Protein Amount (mg/mL) | PEG 8000 (%) | mM $CaCl_2$ | Na acetate (mM) |
|---|---|---|---|---|
| Cif-D129S | 5.0 | 16.0 | 125 | 100 |
| Cif-E153D | 5.0 | 14.0 | 125 | 100 |
| Cif-E153Q | 5.0 | 14.0 | 125 | 100 |
| Cif-H177A | 4.5 | 16.0 | 125 | 100 |
| Cif-H207A | 4.5 | 13.0 | 125 | 100 |
| Cif-Y239F | 5.0 | 15.5 | 125 | 100 |

Upon harvesting for data collection, crystals were soaked in a cryoprotectant composed of the reservoir solution supplemented with 20% (wt/vol) glycerol. The crystals were then flash cooled in the nitrogen stream of an Oxford Cryostream 700 operating at 100 K, or by rapid plunging into a liquid nitrogen bath. Oscillation data were collected at 100 K at the X6A beamline of the National Synchrotron Light Source at Brookhaven National Laboratory. Diffraction images were processed and scaled with the XDS package (Kabsch (1993) J. Appl. Cryst. 26:795-800). Molecular replacement and iterative rounds of automated refinement were carried out with PHENIX (Adams, et al. (2010) Acta Crystallogr. D66:213-221; Adams, et al. (2002) Acta Crystallogr. D58:1948-1954). WinCoot (Emsley & Cowtan (2004) Acta Crystallogr. D60:2126-2132) was used for manual adjustment of the model, and PyMOL was used to generate images of the final model.

Determination of Specific Activity.

Epoxide hydrolase enzyme activity was determined for the reporter substrate epibromohydrin (Sigma) using an adrenochrome reporter assay as described previously (Bahl, et al., (2010) supra; Cedrone, et al. (2005) Biotechnol. Lett. 27:1921-1927; MacEachran, et al. (2008) Infect. Immun. 76:3197-3206). Lipoprotein lipase from Pseudomonas spp. (Sigma) was used as a negative protein control, and a standard curve was generated using 3-bromo-1,2-propanediol (Sigma). The enzyme reaction was carried out using 20 μM protein with 10 mM substrate incubated at 37° C. for 30 minutes. One unit was defined as 1 μmol of substrate hydrolyzed per minute.

Cell Culture.

Parental human bronchial epithelial CFBE41o-cells stably transduced with CFTR (Bebok, et al. (2005) J. Physiol. 569:601-615) were maintained in minimal essential media (Invitrogen) supplemented with 50 U/ml penicillin (Sigma), 50 μg/ml streptomycin (Sigma), 2 mM L-glutamine (Cellgro), 9.1% [vol/vol] fetal bovine serum, 0.5 μg/ml puromycin (InvivoGen), and 5 μg/ml Plasmocin (InvivoGen) at 37° C. with 5% $CO_2$. To establish polarized monolayers, $1 \times 10^6$ cells were seeded onto 24 mm TRANSWELL permeable supports (0.4 μm pore size; Corning) and grown in an air-liquid interface culture at 37° C. with 5% $CO_2$ for 6-9 days prior to use.

Determination of Cell Surface CFTR Levels.

Polarized monolayers of CFBE41o-cells were apically treated with 50 μg of purified Cif protein or a buffer control, and incubated for 1 hour at 37° C. in a 5% $CO_2$ incubator. The relative abundance of CFTR was then determined by biotinylating all cell surface proteins, capturing the surface pool with immobilized streptavidin resin following cell lysis, and probing for CFTR by western blot as previously described (Bomberger, et al. (2011) Methods Mol. Biol. 741:271-283).

The Acid Nucleophile.

Once a substrate is bound, the first step is a nucleophilic attack. Therefore, the predicted nucleophilic Asp at position 129 was targeted for mutation. A structurally and chemically conservative mutation is desirable to minimize any impact on the protein's structure. An Asp to Asn mutation is the most conservative; however, previous studies have shown that a carboxamide at the nucleophile position of an EH can be hydrolyzed by the enzyme to form a carboxylic acid, thus regenerating a functional, wild-type enzyme active site (Pinot, et al. (1995) supra). Therefore, the nucleophile of Cif was mutated to serine, a non-charged polar amino acid whose incorporation at the nucleophile residue position has been shown to be tolerated for other EHs (Pinot, et al. (1995) supra). Recombinantly expressed Cif-D129S protein was purified from E. coli culture supernatant using the same protocol as for wild-type. Cif-D129S crystallized using nearly identical conditions as were used for the wild-type protein (Bahl, et al. (2010) supra). Since the conditions under which a protein will crystallize are strongly dependent upon surface contacts, this indicates that there would be few, if any, structural rearrangements due to the D129S mutation. Diffraction data were collected to 1.55 Å resolution, and phase information obtained by molecular replacement with the wild-type Cif structure as a search model. The final refined model displayed excellent agreement with the diffraction data (see Table 2).

TABLE 2

| | Cif-D129S |
|---|---|
| Data Collection | |
| Wavelength (Å) | 0.9782 |
| Space Group | C2 |
| Unit Cell Dimensions | |
| a, b, c (Å) | 168.2, 84.0, 89.2 |
| α, β, γ (°) | 90, 100.4, 90 |
| Resolution (Å) | 46.08-1.55 (1.59-1.55) |
| $R_{sym}^{b}$ (%) | 5.6 (28.4) |
| $R_{mrgd-F}^{c}$ (%) | 7.5 (30.8) |
| I/σ(I) | 16.9 (4.9) |
| Completeness (%) | 98.0 (96.7) |
| Redundancy | 4.2 (4.2) |
| Refinement | |
| Total number of reflections | 173079 |
| Reflections in the test set | 8686 |
| $R_{work}^{d}/R_{free}^{e}$ (%) | 15.9/17.6 |
| Number of atoms: | |
| Protein | 9551 |
| Solvent | 1224 |
| Ligand | 0 |
| Ramachandran plot$^{f}$ (T) | 91.6/8.0/0.4/0 |
| $B_{av}$ (Å$^2$) | |
| Protein | 12.9 |
| Solvent | 26.8 |
| Bond length RMSD | 0.006 |
| Bond angle RMSD | 1.083 |
| PDB ID | 4DLN |

$^{a}$Values in parentheses are for data in the highest-resolution shell.
$^{b}R_{sym} = \Sigma_h \Sigma_i | I(h) - I_i(h) | \Sigma_h \Sigma_i I_i(h)$, where $I_i(h)$ and $I(h)$ values are the i-th and mean measurements of the intensity of relection h.
$^{c}R_{mrgd-F}$ is robust indicator of the agreement of structure factors of symmetry-related reflections and is described by Diederichs & Karplus (1977) Nat. Struct. Biol. 4(4): 269-75.
$^{d}R_{work} = \Sigma_h | F_{obs}(h) - F_{calc}(h) | \Sigma_h F_{obs}(h)$, he{working set}.
$^{e}R_{free} = \Sigma_h | F_{obs}(h) - F_{calc}(h) | \Sigma_h F_{obs}(h)$, he{test set}.
$^{f}$Core/allowed/generously allowed/disallowed.

A close inspection of the active site demonstrated that a Ser at position 129 could be sterically accommodated. The mutant Ser $O_\gamma$ accepts hydrogen bonds from the backbone amines of Phe63 and Ile130. This feature is similar to the wild-type structure where one $O_\gamma$ of the Asp129 carboxylic acid forms analogous hydrogen bonds, and the other $O_\gamma$ serves as the nucleophile to attack an epoxide substrate. These hydrogen bonds are used to position the side chain of the residue within the active site, and to polarize the Asp carboxylic acid to assist in nucleophile activation. Given that the Cif-D129S mutant positions its side chain pointing toward the protein backbone and away from the substrate, no enzymatic activity was expected. Indeed, enzyme activity was completely abrogated in an assay using the reporter substrate epibromohydrin. Presumably, this mutation should not alter the ability of ring-opening His177 and Tyr239 to bind and coordinate a substrate, nor would it alter the charge relay system. However, by preventing the nucleophilic attack, all detectable enzyme activity was lost.

Furthermore, this effect was not due a conformation change induced by mutation. Alignment of chain A of the Cif-D129S and wild-type models resulted in an RMSD which was lower than the maximum likelihood error estimates for each structure (Table 3). It was therefore concluded that the abrogation of enzyme activity associated with this mutation was solely instigated by the local change in active site functionality.

TABLE 3

| | Maximum-likelihood based coordinate error estimate (Å) | RMSD with wild-type Cif (Å$^2$) |
|---|---|---|
| Cif-D129S | 0.19 | 0.11 |
| Cif-E153D | 0.21 | 0.11 |
| Cif-E153Q | 0.21 | 0.13 |
| Cif-H177A | 0.28 | 0.10 |
| Cif-H207A | 0.21 | 0.12 |
| Cif-Y239F | 0.20 | 0.12 |

The Charge-Relay Acid.

The role of the charge-relay system was subsequently analyzed by mutation of the acid Glu153. Previous studies on the substrate selectivity of Cif have demonstrated that it is an enzyme with unique preferences, although it is most similar to the mammalian EH1 (also known as microsomal EH) (Bahl, et al. (2010) supra). EH1 possesses a catalytic triad, and mutation of the charge relay Glu to Asp resulted in a large increase in the rate of substrate turnover (Arand, et al. (1999) Biochem. J. 337(Pt 1):37-43). While canonical EHs have their charge-relay acid on a loop within the α/β core domain, in Cif this residue is located within a loop that connects the α/β core to the cap domain (Bahl & Madden (2012) supra). This difference alters the directionality of the charge-relay acid, changing the angle and location at which it accepts a hydrogen bond from the catalytic triad His. A detailed structural analysis of the charge-relay acid residue of Cif and other EHs has been described (Bahl & Madden (2012) supra). Although there is currently no structural information available for EH1, sequence alignment clearly reveals that it utilizes a charge-relay acid at the canonical position. In order to thoroughly investigate the charge-relay acid of Cif, the corresponding Glu to Asp mutation was analyzed.

In contrast to EH1, a marked decrease in the specific activity of Cif-E153D was observed. In order to determine if any conformational or structural changes were induced by this mutation, the structure of Cif-E153D was determined (Table 4).

TABLE 4

| | Cif-E153D |
|---|---|
| Data Collection | |
| Wavelength (Å) | 0.9782 |
| Space Group | C2 |
| Unit Cell Dimensions | |
| a, b, c (Å) | 168.4, 84.1, 89.2 |
| α, β, γ (°) | 90, 100.5, 90 |
| Resolution (Å) | 44.07-1.36 (1.45-1.36) |
| $R_{sym}^{b}$ (%) | 7.5 (45.4) |
| $R_{mrgd-F}^{c}$ (%) | 8.5 (39.8) |
| I/σI | 13.6 (3.7) |
| Completeness (%) | 98.7 (97.5) |
| Redundancy | 5.8 (5.8) |
| Refinement | |
| Total number of reflections | 258287 |
| Reflections in the test set | 12908 |
| $R_{work}^{d}/R_{free}^{e}$ (%) | 21.2/22.3 |
| Number of atoms: | |
| Protein | 9451 |
| Solvent | 987 |
| Ligand | 0 |
| Ramachandran plot$^{f}$ (T) | 90.9/8.7/0.4/0 |

TABLE 4-continued

| | Cif-E153D |
|---|---|
| $B_{av}$ (Å$^2$) | |
| Protein | 12.0 |
| Solvent | 22.0 |
| Bond length RMSD | 0.006 |
| Bond angle RMSD | 1.062 |
| PDB ID | 4DM7 |

[a]Values in parentheses are for data in the highest-resolution shell.
[b]$R_{sym} = \Sigma_h \Sigma_i | I(h) - I_i(h) | \Sigma_h \Sigma_i I_i(h)$, where $I_i(h)$ and $I(h)$ values are the i-th and mean measurements of the intensity of relection h.
[c]$R_{mrgd-F}$ is robust indicator of the agreement of structure factors of symmetry-related reflections and is described by Diederichs & Karplus (1977) Nat. Struct. Biol. 4(4): 269-75.
[d]$R_{work} = \Sigma_h | F_{obs}(h) - F_{calc}(h) | \Sigma_h F_{obs}(h)$, hε {working set}.
[e]$R_{free} = \Sigma_h | F_{obs}(h) - F_{calc}(h) | \Sigma_h F_{obs}(h)$, hε {test set}.
[f]Core/allowed/generously allowed/disallowed.

As for Cif-D129S, high quality crystals were generated using conditions similar to those of the wild-type protein, and phase information was obtained by molecular replacement with wild-type Cif as the search model. Upon examination of the refined structure, it was found that no conformational changes were induced upon mutation (Table 3). Asp153 is located at the same position as the wild-type Glu residue, and is also able to form hydrogen bonds with the backbone amides of Gly266 and Met272. However, with a shorter side chain, the Asp is not able to hydrogen bond at the same distances and angles. A finely tuned charge-relay system may require specific interactions between the acid (Glu153) and the base (His297). Perturbation of the acid position would presumably lower the efficacy of this system, which in turn would impair the ability of the enzyme to activate a water molecule to hydrolyze and release the covalent intermediate, thus reducing the specific activity. In the absence of structural information for EH1, it can be speculated that the opposite effects observed by a charge-relay Glu to Asp mutation are somehow due to the positioning of this residue within the protein sequence.

Subsequently, a conservative mutation was introduced to block the function of the charge-relay system of Cif. Gln is polar and sterically similar to the Glu, but does not possess a formal charge. Therefore, a loss of enzyme activity associated with inhibition of the charge-relay system was expected. Indeed, complete abrogation of enzyme activity was observed with Cif-E153Q. Crystallization and structural determination were performed as before (Table 5), and again no mutation was found to induce conformational differences (Table 3).

TABLE 5

| | Cif-E153Q |
|---|---|
| Data Collection | |
| Wavelength (Å) | 1.0000 |
| Space Group | C2 |
| Unit Cell Dimensions | |
| a, b, c (Å) | 168.4, 83.9, 89.5 |
| α, β, γ (°) | 90, 100.4, 90 |
| Resolution (Å) | 46.13-1.66 (1.70-1.66) |
| $R_{sym}^b$ (%) | 9.0 (56.4) |
| $R_{mrgd-F}^c$ (%) | 8.4 (38.5) |
| I/σI | 16.5 (4.1) |
| Completeness (%) | 97.1 (95.8) |
| Redundancy | 7.5 (7.5) |
| Refinement | |
| Total number of reflections | 140462 |
| Reflections in the test set | 7020 |
| $R_{work}^d/R_{free}^e$ (%) | 18.1/20.8 |

TABLE 5-continued

| | Cif-E153Q |
|---|---|
| Number of atoms: | |
| Protein | 9496 |
| Solvent | 870 |
| Ligand | 0 |
| Ramachandran plot[f] (T) | 91.3/8.3/0.4/0 |
| $B_{av}$ (Å$^2$) | |
| Protein | 14.4 |
| Solvent | 24.5 |
| Bond length RMSD | 0.006 |
| Bond angle RMSD | 1.028 |
| PDB ID | 4DMC |

[a]Values in parentheses are for data in the highest-resolution shell.
[b]$R_{sym} = \Sigma_h \Sigma_i | I(h) - I_i(h) | \Sigma_h \Sigma_i I_i(h)$, where $I_i(h)$ and $I(h)$ values are the i-th and mean measurements of the intensity of relection h.
[c]$R_{mrgd-F}$ is robust indicator of the agreement of structure factors of symmetry-related reflections and is described by Diederichs & Karplus (1977) Nat. Struct. Biol. 4(4): 269-75.
[d]$R_{work} = \Sigma_h | F_{obs}(h) - F_{calc}(h) | \Sigma_h F_{obs}(h)$, hε {working set}.
[e]$R_{free} = \Sigma_h | F_{obs}(h) - F_{calc}(h) | \Sigma_h F_{obs}(h)$, hε {test set}.
[f]Core/allowed/generously allowed/disallowed.

Upon examination of the Cif-E153Q structure, it was clear that Gln153 was occupying the same position in the active site as the wild-type Glu residue, including the hydrogen bonds to backbone amides. Although the carboxamide orientation could not be determined directly from X-ray diffraction data, one could be assigned based on the hydrogen bonding profile of this residue. Only the carbonyl oxygen was capable of accepting hydrogen bonds from the backbone amides. Therefore, it could be assumed that the amide group was donating a hydrogen bond to the charge-relay His297. In the wild-type protein, the charge-relay acid accepts a hydrogen bond from His297. By reversing the hydrogen bond orientation between the charge-relay acid and base, activation of a water molecule for release of the enzyme-substrate intermediate was blocked. It was important to note that the E153Q mutation was not expected to impair the ability of the ring-opening residues to bind, coordinate, and assist in epoxide ring opening, nor would it impact the nucleophilic attack on the substrate by Asp129. Therefore, it was expected that all substrates would be converted to suicide inhibitors, and covalent adduction would occur in the presence of the E153Q mutation. Observation of a covalent enzyme-substrate intermediate has been previously demonstrated for other EHs by various techniques (Arand, et al. (1996) *J. Biol. Chem.* 271:4223-4229; Hammock, et al. (1994) *Biochem. Biophys. Res. Commun.* 198:850-856; Muller, et al. (1997) *Eur. J. Biochem.* 245: 490-496; Pinot, et al. (1995) supra), as well as other α/β hydrolase, Asp nucleophile enzymes (Chan, et al. (2011) *J. Am. Chem. Soc.* 133:7461-7468; Pieters, et al. (1999) *Bioorg. Med. Chem. Lett.* 9:161-166).

The Ring-Opening Residues.

Further investigation of the Cif active site continued with mutation of ring-opening residues His177 and Tyr239 to Ala and Phe, respectively. These residues are thought to function together for substrate positioning, serve as electron withdrawing groups for the epoxide oxygen, and donate a proton to the epoxide oxygen to form an alcohol upon ring opening. As such, they were analyzed together.

After performing mutagenesis and protein purification for Cif-H177A and Y239F as before, a complete absence of substrate turnover was observed in the presence of either mutation. It was unclear which residue was responsible for donation of a proton to the epoxide oxygen upon ring opening. It was contemplated that H177 was the more likely candidate due to the generally lower pKa of a His side chain compared to a Tyr. It was again confirmed that the mutations were not altering the protein's conformation by employing the same structure determination pipeline for these Cif mutants. In the wild-type structure, it was observed that a water molecule coordinated by His177 and Tyr239 presumably occupies the position of a substrate epoxide oxygen. It was interesting that this water molecule was still present in the Y239F structure, but was absent with the H177A mutation. These structures were determined to similar resolution (Table 6), so the reason for this was unclear.

TABLE 6

|  | Cif-H177A | Cif-Y239F |
|---|---|---|
| Data Collection |  |  |
| Wavelength (Å) | 0.9770 | 0.9770 |
| Space Group | C2 | C2 |
| Unit Cell Dimensions |  |  |
| a, b, c (Å) | 167.8, 83.8, 89.0 | 168.7, 84.0, 89.3 |
| α, β, γ (°) | 90, 100.4, 90 | 90, 100.5, 90 |
| Resolution (Å) | 45.98-2.12 | 46.18-1.5 |
|  | (2.20-2.12) | (1.61-1.50) |
| $R_{sym}^{b}$ (%) | 9.7 (38.2) | 5.8 (30.2) |
| $R_{mrgd-F}^{c}$ (%) | 14.1 (39.5) | 8.5 (33.4) |
| I/σI | 12.7 (4.0) | 16.1 (4.8) |
| Completeness (%) | 99.8 (99.7) | 97.2 (95.8) |
| Redundancy | 4.2 (4.2) | 4.3 (4.3) |
| Refinement |  |  |
| Total number of reflections | 68795 | 190239 |
| Reflections in the test set | 3454 | 9495 |
| $R_{work}^{d}/R_{free}^{e}$ (%) | 16.6/20.6 | 16.3/18.2 |
| Number of atoms: |  |  |
| Protein | 9340 | 9566 |
| Solvent | 555 | 1250 |
| Ligand | 0 | 24 |
| Ramachandran plot$^{f}$ (T) | 91.3/8.3/0.4/0 | 91.3/8.3/0.4/0 |
| $B_{av}$ (Å$^2$) |  |  |
| Protein | 19.0 | 12.3 |
| Solvent | 26.7 | 25.8 |
| Bond length RMSD | 0.007 | 0.006 |
| Bond angle RMSD | 0.994 | 1.069 |
| PDB ID | 4DMF | 4DMK |

$^a$Values in parentheses are for data in the highest-resolution shell.
$^b$R$_{sym}$ = Σ$_h$Σ$_i$ | I (h) − I$_i$ (h) | Σ$_h$Σ$_i$ I$_i$ (h), where I$_i$ (h) and I (h) values are the i-th and mean measurements of the intensity of relection h.
$^c$R$_{mrgd-F}$ is robust indicator of the agreement of structure factors of symmetry-related reflections and is described by Diederichs & Karplus (1977) Nat. Struct. Biol. 4(4): 269-75.
$^d$R$_{work}$ = Σ$_h$ | F$_{obs}$ (h) − F$_{calc}$ (h) | Σ$_h$ F$_{obs}$ (h), he {working set}.
$^e$R$_{free}$ = Σ$_h$ | F$_{obs}$ (h) − F$_{calc}$ (h) | Σ$_h$ F$_{obs}$ (h), he {test set}.
$^f$Core/allowed/generously allowed/disallowed.

The ring opening pair was also responsible for correctly positioning a substrate for nucleophilic attack. Previous analysis of the Cif-H177Y mutation showed that when the substrate binding position was altered, all EH activity was lost (Bahl & Madden (2012) supra). Taken together, without the ability to bind and coordinate a substrate, or the ability to assist in ring opening, EH activity is inhibited by these mutations.

The Substrate Tunnel His.

The final residue investigated was His207. The sterically defined entrance to the active site of Cif is a funnel lined with a succession of His residues, beginning with ring opening His177, followed by His207, and terminating at the protein surface with His269. To investigate the role of His207 in the catalytic mechanism of Cif, an Ala mutation was generated. Purification of this mutant yielded a 2-fold reduction in the amount of protein produced. Upon assay for epibromohydrin hydrolysis, it was found that the H207A mutation greatly impaired the ability of Cif to function as an EH. However, unlike the residues that directly play a role in catalysis, this mutation did not abrogate all enzyme activity. To examine any conformational impact of this mutation, the structure of Cif-H207A was determined (Table 7), and again no difference in the protein conformation was found.

TABLE 7

|  | Cif-H207A |
|---|---|
| Data Collection |  |
| Wavelength (Å) | 0.9770 |
| Space Group | C2 |
| Unit Cell Dimensions |  |
| a, b, c (Å) | 168.8, 83.8, 89.5 |
| α, β, γ (°) | 90, 100.5, 90 |
| Resolution (Å) | 46.18-1.90 (1.95-1.90) |
| $R_{sym}^{b}$ (%) | 7.0 (33.6) |
| $R_{mrgd-F}^{c}$ (%) | 9.4 (35.4) |
| I/σI | 16.3 (4.4) |
| Completeness (%) | 97.3 (96.3) |
| Redundancy | 4.3 (4.3) |
| Refinement |  |
| Total number of reflections | 94109 |
| Reflections in the test set | 4706 |
| $R_{work}^{d}/R_{free}^{e}$ (%) | 16.2/19.8 |
| Number of atoms: |  |
| Protein | 9491 |
| Solvent | 824 |
| Ligand | 24 |
| Ramachandran plot$^{f}$ (T) | 91.2/8.4/0.4/0 |
| $B_{av}$ (Å$^2$) |  |
| Protein | 15.5 |
| Solvent | 25.6 |
| Bond length RMSD | 0.006 |
| Bond angle RMSD | 1.007 |
| PDB ID | 4DMH |

$^a$Values in parentheses are for data in the highest-resolution shell.
$^b$R$_{sym}$ = Σ$_h$Σ$_i$ | I (h) − I$_i$ (h) | Σ$_h$Σ$_i$ I$_i$ (h), where I$_i$ (h) and I (h) values are the i-th and mean measurements of the intensity of relection h.
$^c$R$_{mrgd-F}$ is robust indicator of the agreement of structure factors of symmetry-related reflections and is described by Diederichs & Karplus (1977) Nat. Struct. Biol. 4(4): 269-75.
$^d$R$_{work}$ = Σ$_h$ | F$_{obs}$ (h) − F$_{calc}$ (h) | Σ$_h$ F$_{obs}$ (h), he {working set}.
$^e$R$_{free}$ = Σ$_h$ | F$_{obs}$ (h) − F$_{calc}$ (h) | Σ$_h$ F$_{obs}$ (h), he {test set}.
$^f$Core/allowed/generously allowed/disallowed.

It was interesting to note that although His207 clearly contributed to epoxide hydrolysis in Cif, it was not conserved with any other known EH. This suggests two possible roles for this residue, highlighted by features unique to the Cif EH. As previously discussed (Bahl & Madden (2012) supra; Bahl, et al. (2010) supra), the active site of Cif is contained at the end of a pocket within the protein. The first likely role of His207 is to interact with the substrate as it traverses the tunnel through the protein to the active site pocket, and its mutation could therefore limit substrate access to the catalytic residues. Secondly, Cif utilizes a His at position 177 as one of the ring-opening residues in place of a canonical Tyr found in all other EHs (Bahl & Madden (2012) supra). Although there do not appear to be any direct hydrogen bond networks between His207 and His177, their close proximity to one another suggests the H207A mutation could be affecting the local pH. Therefore, the H207A mutation could impede the hydrogen bond or proton donating ability of His177, which would result in the observed decrease in epibromohydrin hydrolysis observed with this mutant. These two proposed functions for His207 are not mutually exclusive, as this residue could be contributing to epoxide hydrolysis in multiple ways. However, it is important to note that while His207 is clearly involved in the catalytic mechanism of Cif, a definitive role for this residue cannot be determined from the data presented here.

Additional Observations from the Multiple Cif Mutant Structures.

With such a large array of mutant Cif protein structures, a few additional observations were noted. In the structures of Cif-Y239F and H207A, a glycerol molecule was found coordinated within each active site. Interestingly, clear electron density corresponding to glycerol molecules was not found in any other Cif structure. Additionally, these glycerol molecules were not coordinated at the same position in the different mutants, and there was even some variability across the asymmetric unit of a single mutant. For Cif-Y239F, glycerol was predominantly occupying an open space within the active site pocket, not likely to reflect a catalytically relevant substrate binding site. Alternatively, glycerol was coordinated by the ring-opening residues His177 and Tyr239 in the Cif-H207A structure. This likely reflects the position occupied by a vicinal diol hydrolysis product. Observation of these glycerol molecules illuminates the impact subtle mutations can have on the stereo-selectivity and accessibility of the active site to small molecules.

Another feature discovered was a small shift in the loop containing the β7 hairpin. This results in displacement at the $C_\alpha$ position of residues 170-172, with the maximal shift of ≈5 Å occurring at Gly171. In many of the structures, partial density for an alternate conformation was observed. However, this was not of sufficient quality to model accurately. For others, either the alternate conformation alone, or both were observed. Interestingly, this difference only occurred in one protomer of the Cif dimer. The Cif dimer was not perfectly symmetrical, and the loop shift was only observed with equivalent chains A and C of the asymmetric unit. All of the engineered mutations occurred a minimum distance of ≈8 Å away from this loop, and no residues in between this loop and the site of mutation appeared to shift in any significant way. Therefore, a direct correlation between β7 hairpin loop motion and mutation was not detected. If this conformational sampling were simply stochastic, both conformations in all structures would be expected. It is contemplated that some mutations cause subtle, long range electrostatic effects, and this in turn alters the equilibrium between the two β7 hairpin conformations. Why this only occurs in one protomer of the Cif dimer remains unclear, although it suggests that the alternate conformation is not strongly favored thermodynamically.

Enzyme Activity is Required for the Cellular Effects of Cif.

To examine the relationship between Cif's EH activity and its function as a virulence factor, the panel of mutants were tested for the ability to promote the removal of CFTR from the apical membrane of human airway epithelial cells. Cell surface CFTR abundance was determined by biotinylating all cell surface proteins, capturing this pool with streptavidin, and probing for CFTR via semi-quantitative western blot. It was found that EH enzyme activity was strictly required for the Cif effect. Therefore, it was a logical conclusion that an endogenous human epoxide substrate was also required. It was interesting to note that Cif-E153D and H207A retained some residual levels of enzyme activity, yet they did not exhibit any ability to promote removal of CFTR from the apical membrane of human cells. Either fully wild-type levels of enzyme activity are required for this effect, or these mutations may alter the substrate selectivity of the enzyme and block Cif-mediated hydrolysis of a cellular substrate.

Many human epoxides are potent signaling molecules (Chiamvimonvat, et al. (2007) *J. Cardiovasc. Pharmacol.* 50:225-237; Spector (2009) *J. Lipid Res.* 50 Suppl:S52-56), and therefore the absence of an epoxide could be mediating the effect rather than the generation of a hydrolysis product. Cif-E153Q retained an active nucleophile and was able to attack a substrate, removing it from the cellular pool. However, this can affect only a very small quantity of substrate, as Cif-E153Q will sequester an epoxide substrate stiochiometrically. While a slight decrease in apical CFTR levels were observed with this mutation, the effect was not statistically significant (P=0.1).

Example 2: Identification and Characterization of an Epoxide Hydrolase Inhibitor for *P. aeruginosa* Cif Generation of a CifR Expression Plasmid.

The cifR sequence, from locus PA14_26140, was amplified from *P. aeruginosa* UCBPP-PA14 genomic DNA by PCR using PHUSION high fidelity polymerase (Finnzymes) with the following primers: BspHI_CifR_F (5'-tat atc atg aca acg cga ggc agg cca cgg-3'; SEQ ID NO:1) and BspHI_CifR_R (5'-ggt agt cat gat ggg gcc ctg gaa gag cac ctc cag ggg cca ggc gcg cag cgc ccg tt-3'; SEQ ID NO:2). The PCR product was digested with BspHI and ligated with T4 ligase (NEB) into an NcoI-digested and phosphatase-treated pET16b vector (Novagen). Ligated plasmid was transformed into TOP10 *E. coli* (Invitrogen) and transformants were selected by growth at 37° C. on LB media supplemented with 150 µg/ml ampicillin. Positive clones were verified by DNA sequence analysis. This generated a CifR construct that possesses a carboxy-terminal deca-histidine tag, preceded by a cleavage site for human rhinovirus 3C (HRV-3C) protease: LEVLFQGP (SEQ ID NO:3).

Protein Purification.

Carboxy-terminal hexa-histidine-tagged Cif protein was expressed in TOP10 *E. coli* (Invitrogen) cells and purified by immobilized metal affinity chromatography (IMAC) as described previously (Bahl, et al. (2010) supra). Purified Cif protein was prepared in the following buffer: 100 mM NaCl, 20 mM sodium phosphate (pH 7.4).

CifR protein was also purified by IMAC, with subsequent removal of the histidine affinity tag. ROSETTA 2 DE3 (Novagen) *E. coli* transformed with the CifR expression plasmid were grown in 4 L of 2×YT broth supplemented with 100 µg/ml ampicillin and 34 µg/ml chloramphenicol at 37° C. Expression of CifR protein was then induced at $OD_{600}$=0.6 by addition of isopropyl-β-D-thiogalactopyranoside to 100 µM, and cultures were incubated overnight at 16° C. Cells were harvested from the medium by centrifugation at 5,000 g for 15 minutes at 4° C. Following removal of supernatant, cell pellets were re-suspended in 25 mL of lysis buffer per 1 L of culture volume. The lysis buffer was composed of: 50 mM Tris pH 8.5, 150 mM NaCl, 2 mM $MgCl_2$, 1 mM ATP, 25 units/mL BENZONASE nuclease (Novagen), and 1 EDTA-free Complete Protease Inhibitor Cocktail Tablet (Roche) per 50 mL. Cells were lysed using a French Press, and the lysate clarified by centrifugation at 40,000 RPM for 1 hour at 4° C. in a Ti45 rotor (Beckman). Supernatant was then passed over a 5 mL column of Ni SEPHAROSE resin (GE Healthcare) that had been pre-equilibrated with IMAC buffer composed of: 50 mM Tris pH 8.5, 500 mM NaCl, and 1 mM dithiothreitol (DTT) with 20 mM imidazole pH 8.5. Following a wash with 10 column volumes of IMAC buffer containing 77 mM imidazole to remove unbound material, CifR protein was eluted from the resin over a 15 column volume gradient running from 248 mM to 324 mM imidazole in IMAC buffer. Fractions were pooled, concentrated, and dialyzed into gel filtration buffer containing: 25 mM Tris pH 8.5, 150 mM NaCl, 0.1 mM DTT, and 0.1 mM ATP. The protein concentration was determined by Bradford assay (Biorad), and HRV-3C protease was added to a mass ratio of 1:10 (protease:CifR). Cleavage of the deca-histidine tag proceeded overnight at 4° C. The HRV-3C protease possesses a non-cleavable histidine tag, which is subsequently used to remove it, along with any uncleaved CifR protein, from the sample by passing over a 5 mL column of Ni SEPHAROSE resin (GE). The flow-through was collected, and mature CifR protein was further clarified by size-exclusion chromatography with a HILOAD SUPERDEX 200 prep grade 26/60 column (GE Healthcare) using gel filtration buffer. Purified, matured CifR protein was prepared in: 10 mM Tris pH 8.5, 50 mM KCl, 1 mM DTT, and 5 mM $MgCl_2$.

Epoxide Hydrolase Enzyme Assay.

The radioactivity assay was carried out using tritium-labeled cis-stilbene oxide (CSO) as the substrate as described previously (Gill, et al. (1983) Anal. Biochem. 131:273-82).

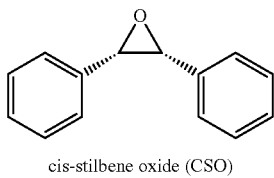 [SMILES: c1ccc([C@H]2O[C@H]2c2ccccc2)cc1]

cis-stilbene oxide (CSO)

The adrenochrome reporter assay was performed as described previously (Bahl, et al. (2010) supra; MacEachran, et al. (2008) supra; Cedrone, et al. (2005) supra) using 1,2-epoxyhexane (Sigma) as the substrate.

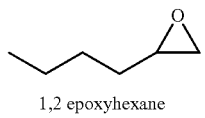

1,2 epoxyhexane

Assays with fluorogenic reporter substrates were carried out as described (Jones, et al. (2005) Anal. Biochem. 343: 66-75; Morisseau, et al. (2011) Anal. Biochem. 414:154-62). For assays using Cyano(6-methoxynaphthalen-2-yl)methyl (oxiran-2-ylmethyl) (CMNGC) as the fluorogenic substrate, measurements were taking using a fluorescent plate reader with $\lambda_{ex}=330$ nm and $\lambda_{em}=465$ nm.

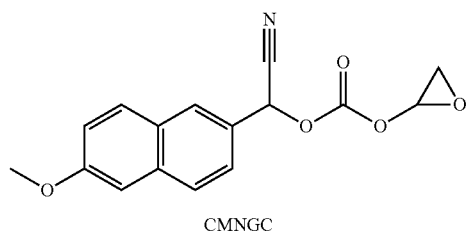 [SMILES: COc1ccc2cc(C(C#N)OC(=O)OC3CO3)ccc2c1]

CMNGC

High Throughput Screening.

All high throughput screening assays were performed using 96-well plates, a 200 μL reaction volume, and a fluorescent plate reader. The primary screen was carried out using 25 μM CMNGC as the fluorogenic reporter substrate, 1 μM Cif protein, test compounds at 10 μM, and 10 μM N,N'-di-(3,4-dichlorophenyl) urea as a positive control for Cif inhibition. The fluorescent signal was measured after allowing the enzyme reaction to proceed for 60 minutes. The secondary screen was performed using the same conditions as the primary screen, except that fluorescent readings were taken every minute for the 60-minute reaction.

Crystallization, Data Collection and Processing, Structure Refinement, and Analysis.

Cif-tiratricol co-crystals were obtained by vapor diffusion against 400 μl of reservoir solution in a 4 μl hanging drop at 291 K (Bahl, et al. (2010) supra). A solution of 8.1 mg/ml Cif protein containing 200 μM tiratricol was mixed in a 1:1 ratio with reservoir solution consisting of 15% (wt/vol) polyethylene glycol 8000, 125 mM $CaCl_2$, 100 mM sodium acetate (pH 5), 200 μM tiratricol, 0.2% (vol/vol) dimethyl sulfoxide (DMSO). Prior to data collection, crystals were washed in cryo solution composed of 15% (wt/vol) polyethylene glycol 8000, 125 mM $CaCl_2$, 100 mM sodium acetate (pH 5), 200 μM tiratricol, 0.2% (vol/vol) DMSO, 20% (wt/vol) glycerol and flash-cooled by plunging into a liquid nitrogen bath. Oscillation data were collected at 100 K at the X6A beamline of the National Synchrotron Light Source at Brookhaven National Laboratory. Diffraction images were processed and scaled with the XDS package (Kabsch (1993) J. Appl. Cryst. 26:795-800). Molecular replacement and iterative rounds of automated refinement were carried out with PHENIX (Adams, et al. (2010) supra; Adams, et al. (2002) supra). WinCoot (Emsley & Cowtan (2004) supra) was used for manual adjustment of the model, and PyMOL was used to generate images of the final model.

Discovery of a First Generation Cif Inhibitor.

The initial screen employed a manually chosen collection of 16 compounds, and enzyme activity of Cif was determined by the radioactivity assay (Table 8). The most promising compounds approached 18% inhibition. The top seven compounds were retested and two chemically related compounds added (Table 8). From the secondary screen, the most potent inhibition was found with N,N'-di-(3,4-dichlorophenyl) urea (DCPU, Entry 18), a compound that inhibited 25%±3% (P=0.004) of Cif enzyme activity.

TABLE 8

| Entry | Chemical Structure | Inhibition (%) |
|---|---|---|
| 1[a] | ethyl cyclohexyl urea | ~2.5 |
| 2 | phenyl urea (N-phenyl-NH$_2$) | 0 |
| 3 | n-pentyl urea | 3 |
| 4 | oleamide | 0 |
| 5 | octylthio-propanamide | 8 |
| 6[b] | 1-adamantyl-N'-(3-carboxypropyl)urea | 0 |
| 7[a] | 1-adamantyl-N'-(10-carboxydecyl)urea | 3 |
| 8 | 1-adamantyl-N'-[4-(2-(2-ethoxyethoxy)ethoxy)butyl]urea | 2.5 |
| 9 | N,N'-diphenylurea | 13 |
| 10 | N-(4-chlorophenyl)-N'-(3,4-dichlorophenyl)urea | 13.5 |
| 11 | 1-adamantyl-N'-(1-acetylpiperidin-4-yl)urea | 2 |

TABLE 8-continued

| Entry | Chemical Structure | Inhibition (%) |
|---|---|---|
| 12 | 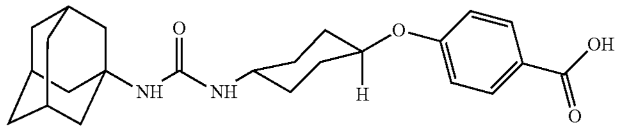 [SMILES: O=C(NC1CCC(Oc2ccc(C(=O)O)cc2)CC1)NC12CC3CC(CC(C3)C1)C2] | 14 |
| 13 | 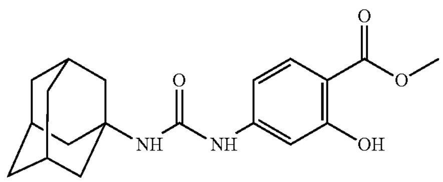 [SMILES: COC(=O)c1ccc(NC(=O)NC23CC4CC(CC(C4)C2)C3)cc1O] | 18 |
| 14 | 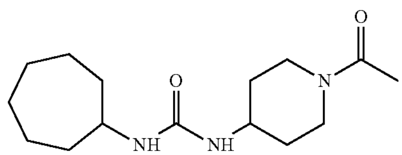 [SMILES: CC(=O)N1CCC(NC(=O)NC2CCCCCC2)CC1] | 6 |
| 15 | 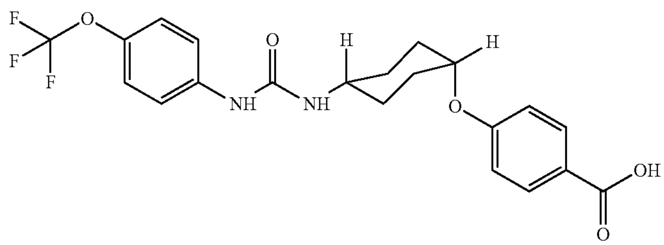 [SMILES: O=C(Nc1ccc(OC(F)(F)F)cc1)NC1CCC(Oc2ccc(C(=O)O)cc2)CC1] | 17 |
| 16 | 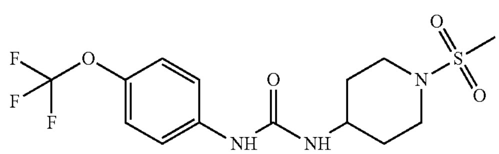 [SMILES: CS(=O)(=O)N1CCC(NC(=O)Nc2ccc(OC(F)(F)F)cc2)CC1] | 14 |
| 17 | 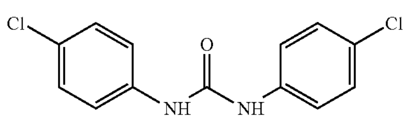 [SMILES: O=C(Nc1ccc(Cl)cc1)Nc1ccc(Cl)cc1] | 7 |
| 18 | 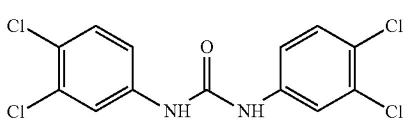 [SMILES: O=C(Nc1ccc(Cl)c(Cl)c1)Nc1ccc(Cl)c(Cl)c1] | 25.5 |

[a]Wolf, et al. (2006) *Anal. Biochem.* 355:71-80.
[b]Gomez, et al. (2006) *Protein Sci.* 15:58-64.

While a compound with detectable inhibition of Cif EH activity was identified out of a minimal library of compounds, this effect was nominal. Attempts to co-crystallize this compound with Cif protein to determine the mechanism of inhibition were unsuccessful, likely due to the poor solubility and weak binding of DCPU to Cif. With a first-hit molecule identified, the next step was to discover a more potent inhibitor. This required significantly expanding the small molecule search space. The radioactivity assay, while useful on a small-scale, was not amenable to large-scale high throughput screening. CSO is a poor substrate for Cif (Bahl, et al. (2010) supra), the assay generates radioactive waste, and the organic extraction step impedes robotic automation. Since no current assay for Cif enzyme activity was compatible with high throughput analysis, a new assay was required.

Design of a High Throughput Enzyme Assay for Cif.

Fluorogenic compounds for mammalian EH2 (also known as soluble EH; Jones, et al. (2005) supra) have previously been used for high throughput screening for enzyme inhibitors (Xie, et al. (2009) *Bioorg. Med. Chem. Lett.* 19:2354-9). These compounds contain an epoxide moiety adjacent to an ester, which in turn is linked to a proto-fluorophore. Upon epoxide hydrolysis, the newly generated vicinal-diol undergoes intramolecular cyclization with the adjacent ester, cleaving off a compound that quickly decays to produce a fluorophore (Jones, et al. (2005) supra).

Cif was tested for its ability to cleave the EH2 fluorogenic substrates; however, a fluorescent signal above the background was not detectable.

As an EH, Cif possesses a unique substrate selectivity profile. Based on previous work, Cif appears to prefer terminal, generally mono-substituted epoxide substrates (Bahl, et al. (2010) supra). While CSO is disubstituted, the epoxide moiety is physically located at the end of the molecule due to the cis bond. Existing EH2 fluorogenic substrates possess di-substituted epoxide moieties, and may be incompatible with Cif for this reason. To investigate if Cif can hydrolyze the epoxy-ester portion of a fluorogenic compound where the epoxide is mono-substituted, hydrolysis of glycidyl methacrylate and allyl glycidyl ether using the adrenochrome reporter assay was determined. Cif was capable of hydrolyzing these substrates, and therefore seemed likely be able to hydrolyze a fluorogenic epoxide substrate with a terminal epoxide molecule. In parallel, a series of fluorogenic epoxide substrates were designed to possess a mono-substituted epoxide moiety, which have proven useful with mammalian EH1 (also known as microsomal EH; Morisseau, et al. (2011) supra). Therefore, Cif was examined for the ability to catalyze their hydrolysis. It was found that Cif could act on each of these compounds, and optimal signal was achieved using CMNGC. Additionally, the fluorescent signal was completely lost in the presence of the D129S mutation, which was shown herein to abrogate all enzyme activity of Cif. Assay conditions were then optimized for high throughput screening.

High Throughput Screening for Cif Inhibitors.

Toxicity is often a limiting factor when developing small molecules for clinical use. While no toxicology has yet been performed on DCPU, as a polychlorinated aromatic it is unlikely to be well-tolerated by mammalian cells. For a second generation Cif inhibitor, a molecule with limited toxicity and the potential for immediate clinical application was sought. A library of 1600 FDA-approved compounds was screened for Cif inhibitory activity. Upon performing the primary screen, low signal-to-background and high signal-to-noise ratios were observed. In addition, excellent Z' values were found using DCPU as a positive control for inhibition. Taken together with the low intraplate variability of the positive control samples, these metrics indicate a robust assay for Cif inhibition (Table 9). These statistical parameters are commonly used to evaluate high throughput screening assays, and have been described in detail (Zhang, et al. (1999) J. Biomol. Screen 4:67-73).

TABLE 9

| Plate# | Total Activity Control | | | Positive Control Inhibitor | | |
|---|---|---|---|---|---|---|
| | S/B[a] | S/N[b] | Z'[c] | % I[d] | SD[e] | Z[c] |
| 1 | 3.1 | 60.2 | 0.68 | 20.9 | 1.3 | 0.71 |
| 2 | 2.9 | 99.8 | 0.75 | 30.0 | 0.5 | 0.86 |
| 3 | 3.0 | 44.4 | 0.76 | 14.0 | 0.3 | 0.77 |
| 4 | 2.9 | 78.5 | 0.78 | 15.9 | 0.8 | 0.74 |
| 5 | 2.8 | 65.3 | 0.72 | 14.6 | 0.7 | 0.78 |
| 6 | 2.9 | 71.4 | 0.83 | 30.0 | 1.1 | 0.79 |
| 7 | 3.0 | 48.3 | 0.82 | 19.8 | 0.5 | 0.74 |
| 8 | 2.9 | 62.6 | 0.80 | 26.0 | 1.1 | 0.72 |
| 9 | 3.0 | 54.1 | 0.87 | 15.7 | 0.2 | 0.82 |
| 10 | 2.9 | 138.2 | 0.79 | 20.7 | 0.7 | 0.78 |
| 11 | 2.9 | 123.1 | 0.86 | 24.8 | 0.6 | 0.87 |
| 12 | 2.8 | 145.3 | 0.83 | 19.0 | 0.7 | 0.83 |
| 13 | 2.9 | 59.7 | 0.87 | 15.2 | 0.2 | 0.84 |
| 14 | 2.9 | 143.3 | 0.89 | 17.9 | 0.4 | 0.86 |
| 15 | 2.9 | 49.1 | 0.87 | 25.0 | 1.7 | 0.70 |
| 16 | 3.1 | 79.1 | 0.86 | 15.2 | 0.5 | 0.75 |
| 17 | 2.9 | 94.8 | 0.80 | 24.3 | 0.9 | 0.79 |
| 18 | 2.9 | 89.7 | 0.88 | 17.3 | 0.6 | 0.75 |
| 19 | 2.9 | 81.7 | 0.91 | 17.2 | 0.5 | 0.82 |
| 20 | 2.9 | 69.5 | 0.91 | 20.1 | 0.6 | 0.83 |
| Average | 2.9 | 83 | 0.82 | 20 | 0.7 | 0.79 |
| SD[e] | 0.1 | 32 | 0.06 | 5 | | 0.05 |

Statistical parameters utilized herein are described in detail by Zhang et al. (1999) supra.
[a]S/B = signal-to-background ratio.
[b]S/N = signal-to-noise ratio.
[c]Z' is a statistical parameter indicative of assay robustness and reproducibility.
[d]% I = percent of the total enzyme activity inhibited.
[e]SD = standard deviation.
[f]Z = screening window coefficient.

The screen was performed with only a 10-fold stoichiometric excess of inhibitor over Cif enzyme. Therefore, the threshold for a positive hit was set at the relatively low value of 30% inhibition. Using this criterion 47 compounds were identified, yielding a 2.9% hit rate (Table 10).

TABLE 10

| Plate | % Inhibition | Compound Name |
|---|---|---|
| 1 | 48 | Mefenamic acid |
| 2 | 31 | Enalapril maleate |
| 2 | 34 | Ketoprofen |
| 2 | 32 | Cefoxitin sodium |
| 3 | 36 | Canrenone |
| 4 | 86 | Benserazide hydrochloride |
| 5 | 71 | Equilin |
| 5 | 39 | Estradiol |
| 6 | 32 | Eugenol |
| 6 | 31 | Fluorometholone |
| 6 | 48 | Ibuprofen |
| 6 | 32 | Mercaptopurine |
| 7 | 42 | Sulfadiazine |
| 7 | 40 | Tobramycin |
| 8 | 35 | Triamterene |
| 8 | 32 | Warfarin |
| 9 | 33 | Betaine hydrochloride |
| 9 | 33 | Triflupromazine hydrochloride |
| 11 | 32 | Flunixin meglumine |
| 11 | 47 | Acarbose |
| 11 | 79 | Azaperone |
| 11 | 48 | Azelastine hydrochloride |
| 12 | 31 | Toremiphene citrate |
| 12 | 34 | Pregnenolone succinate |
| 12 | 66 | Desoxymetasone |
| 13 | 33 | Buspirone hydrochloride |
| 14 | 52 | Ethanolamine oleate |
| 14 | 36 | Dimethyl fumarate |
| 14 | 34 | Modaline sulfate |
| 14 | 46 | Thiostrepton |
| 14 | 51 | Clomipramine hydrochloride |
| 14 | 36 | Tilorone |
| 14 | 35 | Saxagliptin |
| 15 | 34 | Gadoteridol |
| 15 | 43 | Clofarabine |
| 15 | 35 | Vorinostat |
| 15 | 38 | Algestone acetophenide |
| 15 | 45 | Penciclovir |
| 16 | 41 | Candicidin |
| 18 | 46 | Protoporphyrin ix |
| 18 | 42 | Octopamine hydrochloride |
| 19 | 86 | Tiratricol |
| 19 | 43 | Edaravone |
| 20 | 78 | Sodium tetradecyl sulfate |
| 20 | 47 | Merbromin |
| 20 | 44 | Cetrimonium bromide |
| 20 | 34 | Miltefosine |

Four of the compounds identified in the primary screen were shown to quench the fluorescent signal generated by the assay, and thus were not selected for further evaluation. Subsequently, the filtered primary hits were retested to validate the observed inhibitory effect. After performing the secondary screen in sextuplicate (Table 11), robust indicators of assay quality were again observed (Table 12).

TABLE 11

| Compound Name | % Inhibition | | | | | | |
|---|---|---|---|---|---|---|---|
| | 1* | 2* | 3* | 4* | 5* | 6* | Mean ± SD |
| Mefenamic acid | 5 | 24 | 17 | 22 | 20 | 6 | 16 ± 8 |
| Enalapril maleate | −6 | 13 | 1 | 9 | 10 | −3 | 4 ± 8 |
| Ketoprofen | 2 | 14 | 9 | 8 | 15 | 4 | 9 ± 5 |
| Cefoxitin sodium | −3 | 16 | 5 | 9 | 19 | 14 | 10 ± 8 |
| Canrenone | 16 | 27 | 20 | 24 | 28 | 27 | 24 ± 5 |
| Benserazide hydrochloride | 77 | 85 | 80 | 74 | 78 | 80 | 79 ± 4 |
| Estradiol | 4 | 5 | 5 | 6 | 8 | −6 | 4 ± 5 |
| Eugenol | 4 | 0 | 7 | 4 | 6 | −4 | 3 ± 4 |
| Fluorometholone | 18 | 15 | 19 | 16 | 21 | 16 | 18 ± 2 |
| Ibuprofen | 1 | 6 | 5 | 8 | 15 | 7 | 7 ± 5 |
| Mercaptopurine | 5 | 15 | 19 | 15 | 15 | 11 | 13 ± 5 |
| Sulfadiazine | 23 | 24 | 24 | 26 | 28 | 15 | 23 ± 4 |
| Tobramycin | −5 | −7 | −5 | −12 | 0 | −21 | −8 ± 7 |
| Triamterene | 15 | 17 | 18 | 21 | 28 | 16 | 19 ± 5 |
| Warfarin | 12 | 12 | 17 | 15 | 20 | 17 | 15 ± 3 |
| Betaine hydrochloride | 6 | 10 | 9 | 17 | 20 | 18 | 13 ± 6 |
| Triflupromazine hydrochloride | 4 | 10 | −2 | 1 | 8 | −6 | 2 ± 6 |
| Flunixin meglumine | 13 | 15 | 14 | 18 | 19 | 4 | 14 ± 5 |
| Azelastine hydrochloride | 30 | 31 | 33 | 34 | 42 | 30 | 34 ± 4 |
| Toremiphene citrate | 3 | 7 | 13 | 12 | 15 | 11 | 10 ± 4 |
| Pregnenolone succinate | 6 | 12 | 8 | 13 | 17 | 15 | 12 ± 4 |
| Desoxymetasone | 34 | 42 | 34 | 40 | 42 | 41 | 39 ± 4 |
| Buspirone hydrochloride | 0 | −3 | 0 | −1 | −2 | −11 | −3 ± 4 |
| Ethanolamine oleate | 5 | 7 | 8 | 9 | 12 | 0 | 7 ± 4 |
| Dimethyl fumarate | 3 | −2 | 8 | 7 | 9 | 6 | 5 ± 4 |
| Modaline sulfate | 10 | 7 | 12 | 12 | 13 | 17 | 12 ± 3 |
| Thiostrepton | 14 | 15 | 25 | 27 | 43 | 42 | 28 ± 12 |
| Clomipramine hydrochloride | 0 | 3 | 9 | 3 | 9 | 7 | 5 ± 4 |
| Tilorone | 4 | 5 | 5 | 11 | 10 | 0 | 6 ± 4 |
| Saxagliptin | 5 | 0 | 6 | 6 | 11 | 3 | 5 ± 4 |
| Gadoteridol | 7 | 3 | 10 | 13 | 16 | 15 | 11 ± 5 |
| Clofarabine | 7 | 8 | 7 | 13 | 20 | 16 | 12 ± 5 |
| Vorinostat | 5 | 13 | 8 | 14 | 18 | 22 | 13 ± 6 |
| Algestone acetophenide | −5 | −2 | 0 | −2 | 3 | −10 | −3 ± 5 |
| Penciclovir | −11 | 1 | 2 | 3 | 7 | −3 | 0 ± 6 |
| Candicidin | 3 | 13 | 17 | 19 | 23 | 18 | 15 ± 7 |
| Protoporphyrin ix | 12 | 16 | 21 | 18 | 28 | 29 | 20 ± 7 |
| Octopamine hydrochloride | 1 | 6 | 12 | 9 | 18 | 17 | 11 ± 6 |
| Tiratricol | 72 | 71 | 72 | 74 | 77 | 78 | 74 ± 3 |
| Edaravone | 21 | 13 | 13 | 26 | 19 | 6 | 16 ± 7 |
| Sodium tetradecyl sulfate | 9 | 4 | 12 | 12 | 13 | 5 | 9 ± 4 |
| Cetrimonium bromide | 1 | −1 | −4 | 3 | 8 | 2 | 2 ± 4 |
| Miltefosine | 4 | 3 | 11 | 10 | 11 | 11 | 8 ± 4 |

*Plate number.

TABLE 12

| Plate # | Total Activity Control | | |
|---|---|---|---|
| | S/B[a] | S/N[b] | Z'[c] |
| 1 | 2.5 | 55.3 | 0.85 |
| 2 | 2.6 | 38.6 | 0.80 |
| 3 | 2.6 | 40.1 | 0.75 |
| 4 | 2.5 | 99.8 | 0.76 |
| 5 | 2.5 | 107.3 | 0.94 |
| 6 | 2.4 | 56.8 | 0.73 |
| Average | 2.5 | 66 | 0.81 |
| SD[e] | 0.1 | 30 | 0.08 |

In order to more rigorously identify compounds suitable for further characterization, the threshold for a positive hit was increased to 50% inhibition. The culmination of the screening efforts identified two compounds: benserazide-HCl and 3,3',5-triiodothyroacetic acid (tiratricol).

Biochemical Characterization of Cif Inhibitors.

The first step in characterizing the two compounds identified by high throughput screening was to verify that the inhibition was reproducible using fresh preparations. Chemical libraries are often stored for extended periods of time, which can lead to breakdown products contributing to the assay outcome. While the inhibition observed with a fresh tiratircol solution was consistent with the primary and secondary screening results, a fresh benserazide-HCl solution lost all observable inhibition. Additionally, it was noticed that benserazide-HCl solutions, either aqueous or in DMSO, acquired a red color over time, suggesting that the compound was susceptible to breakdown.

After aging the freshly prepared benserazide-HCl solution for 3 months at room temperature, Cif inhibition was retested. Once more, there was no detectable inhibition. Cocrystallization of Cif protein with the red benserazide hydrochloride breakdown solution resulted in crystals with an enriched color over the well solution, indicating that the chromophore had some affinity for Cif protein. However, clear electron density was not obtainable for any additional compounds bound specifically to Cif. This observation could either be due to low occupancy of a molecule bound to Cif, or a non-specific interaction. 1D proton NMR revealed that a large number of additional peaks were present in the spectra of the breakdown sample. LC/MS analysis detected >100 additional compounds present after aging a benserazide-HCl solution in water. Due to the high diversity of products generated by benserazide-HCl breakdown, as well as the inability to repeat inhibition of Cif EH enzyme activity, this compound was not further investigated.

After successfully recapitulating Cif inhibition with fresh tiratricol, the effect was confirmed with an independent substrate and assay. Using the adrenochrome reporter assay and epoxyhexane, an epoxide substrate previously shown to be hydrolyzed by Cif, a robust inhibition of Cif enzyme activity was observed.

Subsequently, tiratricol inhibition was characterized kinetically, once again using the fluorogenic substrate CMNGC. The $K_i$ was found to be 4.1±0.4 µM. Additionally, the $K_i$ was independent of substrate concentration, indicating that tiratricol functioned via a non-competitive mechanism of inhibition.

Structural Studies of Tiratricol Bound to Cif.

To further illuminate the mechanism of inhibition, Cif was crystallized in the presence of tiratricol. A serendipitous benefit of using tiratricol with X-ray diffraction experiments was the presence of three iodine atoms in the compound which could be used to obtain an anomalous signal. Oscillation data for Cif-tiratricol co-crystals were collected at both native and anomalous wavelengths (Table 13).

TABLE 13

| | Wild-Type Cif/Tiratricol | |
|---|---|---|
| Data Collection | | |
| Wavelength (Å) | 1.0000 | 1.7220 |
| Space Group | C2 | C2 |
| Unit Cell Dimensions | | |
| a, b, c (Å) | 169.7, 84.0, 89.5 | 170.0, 84.4, 89.7 |
| α, β, γ (°) | 90, 100.5, 90 | 90, 100.5, 90 |
| Resolution (Å) | 42.23-1.75 | 46.50-2.03 |
| | (1.80-1.75) | (2.08-2.03) |
| $R_{sym}{}^b$ (%) | 8.1 (35.9) | 9.4 (26.2) |
| $R_{mrgd-F}{}^c$ (%) | 10.2 (38.9) | 6.4 (26.2) |
| I/σ (I) | 12.4 (3.7) | 14.2 (4.7) |
| Completeness (%) | 100.0 (100.0) | 98.9 (86.0) |
| Redundancy | 4.2 (4.2) | 7.1 (4.5) |
| $SigAno^d$ | | 0.85 (0.71) |
| Refinement | | |
| Total number of reflections | 124409 | |
| Reflections in the test set | 6197 | |
| $R_{work}{}^e/R_{free}{}^f$(%) | 16.4/19.5 | |
| Number of atoms: | | |
| Protein | 9427 | |
| Solvent | 1168 | |
| Ligand | 84 | |
| Ramachandran plot$^g$ (T) | 91.0/8.6/0.4/0 | |
| $B_{av}$ (Å$^2$) | | |
| Protein | 13.6 | |
| Solvent | 28.2 | |
| Bond length RMSD | 0.007 | |
| Bond angle RMSD | 1.105 | |

$^a$Values in parentheses are for data in the highest-resolution shell. $^bR_{sym} = \Sigma_h\Sigma_i \mid I (h) - I_i (h) \mid \Sigma_h\Sigma_i I_i (h)$, where $I_i$ (h) and I (h) values are the i-th and mean measurements of the intensity of relection h.
$^cR_{mrgd-F}$ is robust indicator of the agreement of structure factors of symmetry-related reflections and is described by Diederichs & Karplus (1977) Nat. Struct. Biol. 4(4): 269-75.
$^dSigAno = <\mid F(+) - F(-) \mid \sigma_A> {}^eR_{work} = \Sigma_h \mid F_{obs} (h) - F_{calc} (h) \mid \Sigma_h F_{obs} (h)$, hε {working set}.
$^fR_{free} = \Sigma_h \mid F_{obs} (h) - F_{calc} (h) \mid \Sigma_h F_{obs} (h)$, hε {test set}.
$^g$Core/allowed/generously allowed/disallowed.

An isomorphous difference map calculated against the apo-protein also revealed the prominent peaks per Cif molecule. An anomalous electron density map also exhibited three strong peaks per Cif molecule at the same positions observed in the difference map. Prior to inclusion in the model, a $2F_o-F_c$ map displayed unambiguous electron density for tiratricol bound within the active site tunnel of Cif, and the iodine positions were consistent with the anomalous and isomorphous difference peaks. Tiratricol binding occludes the tunnel by which a substrate enters the active site of Cif, preventing substrates from reaching the catalytic machinery. As tiratricol and an epoxide substrate bind at distinct sites within the protein, this finding is consistent with the kinetic observation of a non-competitive inhibition.

Furthermore, the tiratricol bound structure of Cif revealed the mechanism by which access to the active site is gated. In the apo structure of Cif (PDB ID 3KD2), no direct pathway to the active site was entirely present. The location of this tunnel based on the most accessible route to the protein surface has been predicted. However, this route is constricted to be <0.5 Å wide at the narrowest point. This opening is smaller than the van der Waals radius of carbon, indicating that it is not broad enough for a substrate to traverse in this conformation. Tiratricol binding captured the open conformation of this tunnel. Gating appeared to be controlled by three residues: Phe164, Leu174, and Met272. These residues form a gasket that can restrict access to the active site, and may also act as a selectivity filter for epoxide substrates. Through their motion, the tunnel opens to create a ≥3.4 Å wide passageway. It was interesting to note that there only appeared to be two prominent interactions between Cif and tiratricol. The first was a hydrogen bond to the backbone carbonyl of Gly270. The second was with gating residue Phe164, which had rotated the phenyl group of its side chain to participate in a π-stacking interaction with an aromatic ring of tiratricol.

The Effect of Tiratricol on Cif Expression by P. Aeruginosa.

Cif is expressed by P. aeruginosa as part of a three gene operon. This operon is negatively regulated by CifR, an epoxide sensitive TetR family repressor (MacEachran, et al. (2008) supra). CifR binds to DNA and prevents the transcriptional machinery from accessing the promoter for the Cif operon. Upon exposure to an epoxide containing molecule, CifR releases DNA, resulting in increased transcription of the Cif operon and increased Cif protein production. It has been previously shown that Cif and CifR have overlapping substrate/ligand specificities (MacEachran, et al. (2008) supra). Therefore, it is important to consider any potential Cif inhibitor in the context of the bacterial response. If an inhibitor were to trigger P. aeruginosa to produce more Cif, the inhibitor concentrations could potentially be overwhelmed by excess Cif protein. To investigate this possibility, tiratricol was tested for the ability to bind CifR and promote its release from DNA by means of an in vitro DNA binding assay. Tiratricol caused CifR to release from DNA as efficiently as a previously characterized epoxide ligand. This was not unexpected considering that many TetR family repressors have broad ligand binding specificities as well as multiple ligand binding sites (Schumacher & Brennan (2003) Res. Microbiol. 154:69-77). An important factor in determining if an exogenous compound will induce gene expression is its accessibility to the bacterial cytosol. Therefore, Cif protein levels were examined after P. aeruginosa was exposed to tiratricol. In contrast to the in vitro DNA binding assay result, there was no detectable increase in Cif expression using this in vivo model.

Example 3: Structure Activity Relationship Analysis of Tiratricol

Table 14 lists the activity of various tiratricol analogs for inhibiting Cif.

TABLE 14

| Entry | Structure | MW g/mol | CIF IC$_{50}$ (µM)$^a$ |
|---|---|---|---|
| Tiratricol | I | 621.8 | 4.7 ± 0.6 |

TABLE 14-continued

| Entry | Structure | MW g/mol | CIF IC$_{50}$ (μM)[a] |
|---|---|---|---|
| 1 | 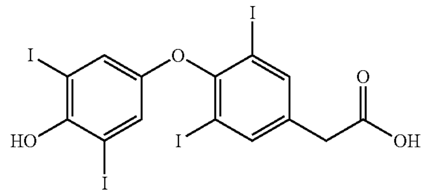 [SMILES: O=C(O)Cc1cc(I)c(Oc2cc(I)c(O)c(I)c2)c(I)c1] | 747.8 | 20 ± 2 |
| 2 | 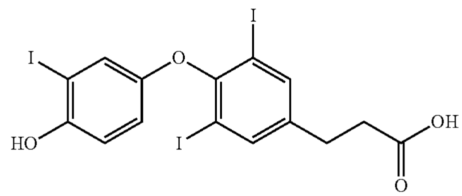 [SMILES: O=C(O)CCc1cc(I)c(Oc2ccc(O)c(I)c2)c(I)c1] | 635.8 | 4.4 ± 0.5 |
| 3 | 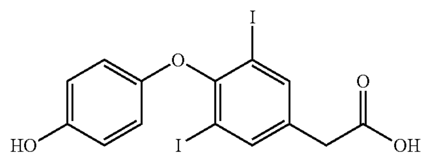 [SMILES: O=C(O)Cc1cc(I)c(Oc2ccc(O)cc2)c(I)c1] | 496.0 | 100 ± 2 |
| 4 | 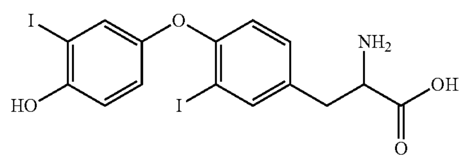 [SMILES: NC(Cc1ccc(Oc2ccc(O)c(I)c2)c(I)c1)C(=O)O] | 525.1 | 80 ± 10 |
| 5 | 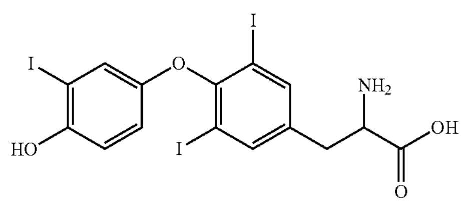 [SMILES: NC(Cc1cc(I)c(Oc2ccc(O)c(I)c2)c(I)c1)C(=O)O] | 651.0 | 21 ± 2 |
| 6 | 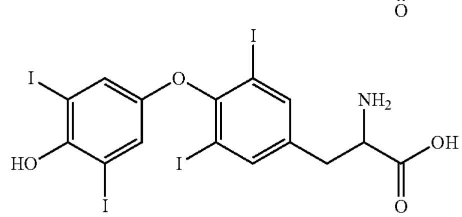 | 776.9 | >100 |
| 7 | 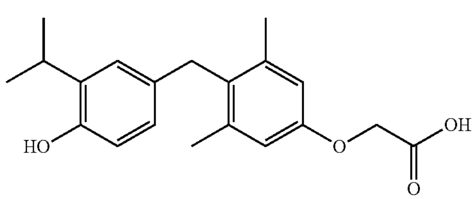 [SMILES: Cc1cc(OCC(=O)O)cc(C)c1Cc1ccc(O)c(C(C)C)c1] | 328.4 | >100 |
| 8[b] | 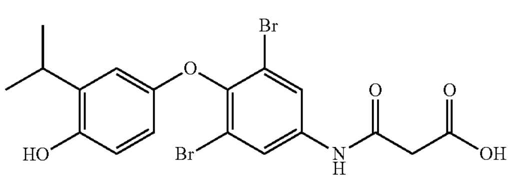 [SMILES: CC(C)c1cc(Oc2c(Br)cc(NC(=O)CC(=O)O)cc2Br)ccc1O] | 487.1 | 2.7 ± 0.4 |

TABLE 14-continued

| Entry | Structure | MW g/mol | CIF IC$_{50}$ (µM)$^a$ |
|---|---|---|---|
| 9 | (4-hydroxyphenyl phenyl ether) | 186.2 | >100 |
| 10 | (4-aminophenyl phenyl ether) | 185.2 | >100 |
| 11 | (4-phenoxybenzoic acid) | 214.2 | >100 |

Conditions:
[E] = 0.6 µM;
[S] = 25 µM;
37° C. for 15 minutes;
pre-incubation 5 minutes at 37° C.
$^a$average ± standard deviation (n = 3).
$^b$also known as KB2115 (Karo Bio).

This analysis indicated that the addition or removal of an iodine to tiratricol (entries 2 and 4) reduced potency. While having a longer acid arm (entry 3) did not change the potency, addition of an amine (entries 5 and 6) reduced potency. Simple molecules without side chains (entries 9 to 11) did not exhibit any inhibition. In addition, thyroid hormone mimetics (entries 7 and 8) were tested and while the activity of entry 7 was not good, entry 8 was very good.

Example 4: Additional Cif Inhibitors

To identify additional inhibitors of the Cif enzyme, further screening assays were conducted. The results of these screens identified two additional classes of Cif inhibitors: urea-based scaffolds and endogenous epoxide scaffolds.

Urea-Based Scaffolds.

A screen of soluble expoxide hydrolase (sHE) inhibitors identified the urea-based scaffold shown in Table 15.

TABLE 15

| Entry | Inhibition at 10 µM (%) | CIF IC$_{50}$ (µM) | HsEH IC$_{50}$ (nM) | Structure |
|---|---|---|---|---|
| 1 | 41 | >100 | 3.8 | (adamantyl-urea-phenyl propanoate) |
| 2 | 41 | NA | | (2,6-dimethylphenyl urea cyclohexyl 2,6-difluorobenzyl ether) |
| 3 | 39 | 1.8 ± 0.4 | | (2,6-difluorobenzoyl urea 3,5-dimethylphenyl) |

TABLE 15-continued

| Entry | Inhibition at 10 μM (%) | CIF IC$_{50}$ (μM) | HsEH IC$_{50}$ (nM) | Structure |
|---|---|---|---|---|
| 4 | 50 | 1.5 ± 0.3 | | 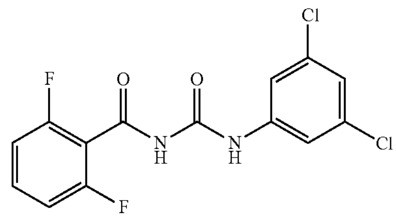 [SMILES: O=C(NC(=O)c1c(F)cccc1F)Nc1cc(Cl)cc(Cl)c1] |
| 5 | 39 | >100 | | 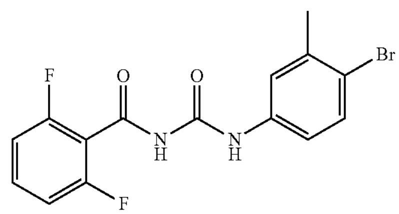 [SMILES: Cc1cc(NC(=O)NC(=O)c2c(F)cccc2F)ccc1Br] |
| 6 | 38 | >100 | | 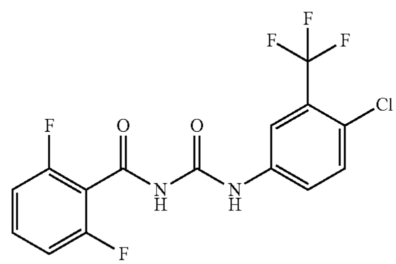 [SMILES: O=C(NC(=O)c1c(F)cccc1F)Nc1ccc(Cl)c(C(F)(F)F)c1] |
| 7 | 40 | >100 | | 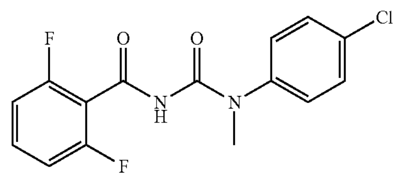 [SMILES: CN(C(=O)NC(=O)c1c(F)cccc1F)c1ccc(Cl)cc1] |
| 8 | 44 | N.A. | 33300 | 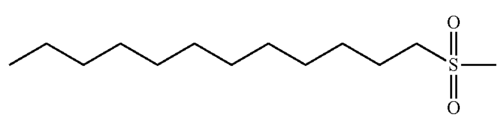 [SMILES: CCCCCCCCCCCCS(C)(=O)=O] |
| 9 | 38 | 7.4 ± 0.6 | 100000 | 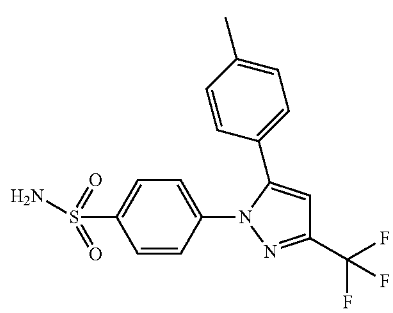 [SMILES: Cc1ccc(-c2cc(C(F)(F)F)nn2-c2ccc(S(N)(=O)=O)cc2)cc1] |
| 10 | 44 | 40 ± 6 | 38 | 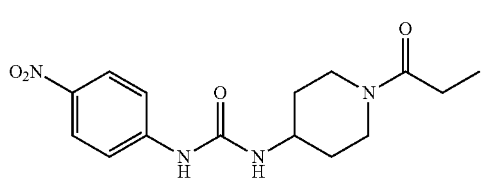 [SMILES: CCC(=O)N1CCC(NC(=O)Nc2ccc([N+](=O)[O-])cc2)CC1] |

The results of this analysis indicated that entries and 4 exhibited IC$_{50}$ values even more potent than tiratricol.

Endogenous Epoxide Scaffolds.

Detailed kinetic information on the interaction of Cif with an endogenous arachidonic acid-derived signaling epoxide, 14,15-EET (14,15-epoxyeicosa-5,8,11-trienoic acid), was also obtained.

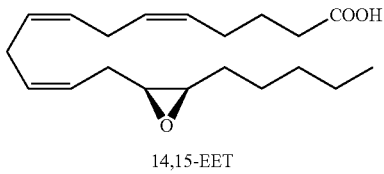 [SMILES: CCCCC[C@H]1O[C@H]1C/C=C\C/C=C\C/C=C\CCCC(=O)O]

14,15-EET

Specifically, three concentrations of 14,15-EET were used (0.5, 5 and 50 µM), along with two different incubation times (90 and 180 minutes) and a low enzyme concentration ([E]=0.2 µM). The results were similar at 90 and 180 minutes, confirming that the assay was within the linear range of catalysis. Less than 5% of the substrate was converted: [S]=0.5 µM, v=0.003 pmol/minute; [S]=5 µM, v=0.02 pmol/minute; and [S]=50 µM, v=1.2 pmol/minute.

Similar analysis was carried out with various other monoepoxide fatty acids and derivatives therefore, including 9(10)-EpOME, 11(12)-EET, 11(12)-EET methyl ester, 12(13)-EpOME, 14(15)-EE-5(Z)-E, 14(15)-EET-sulfonimide (SI), 14(15)-EET ethanolamide, 16(17)-EpDPE, 14(15)-EpETE, 14(15)-EET, 17(18)-EpETE, and 19(20)-EpDPE. The results of this analysis are presented in FIG. 1.

Example 5: Rational Design of Potent and Selective Inhibitors of Cif

General Methodology.

All reagents and solvents were purchased from commercial suppliers and were used without further purification. KB2115 was purchased from Cayman Chemicals (Purity ≥98%). All reactions were performed in an inert atmosphere of dry nitrogen or argon. Melting points were determined using an OPTIMELT melting point apparatus. $^1$H and $^{13}$C-NMR spectra were collected using a Varian 600, 400 or 300 MHz spectrometer with chemical shifts reported relative to residual deuterated solvent peaks or a tetramethylsilane internal standard. Accurate masses were measured using a Micromass LCT ESI-TOF-MS. The purity of the compounds that were tested in the assay was determined by reverse phase HPLC-DAD and found to be >95% at 254 nm absorption. Reactions were monitored on thin-layer chromatography (TLC) plates (silica gel matrix, fluorescent indicator, Sigma-Aldrich), and spots were either monitored under UV light (254 mm) or stained with phosphomolybdic acid. The same TLC system was used to test purity, and all final products showed a single spot on TLC and when measured gave a sharp melting point.

General Procedure A: S$_N$Ar.

To an ice-cold dimethylformamide (DMF) solution of phenol 2 (1.1 equiv) was slowly added 1 M NaOH$_{aq}$ (1.1 equiv), followed by compound 3 (1.0 equiv) in DMF. The reaction was slowly warmed up to room temperature, and stirred for 1-24 hours. To this solution was added water. The mixture was extracted with hexane/ethyl acetate (5:1) mixture three times. The organic layer was combined, washed with brine, dried over MgSO$_4$, filtered and concentrated in vacuo.

General Procedure B: Deprotection of Methoxy Moiety.

To an ice-cold dichloromethane (DCM) solution of diphenylether 4, 1 M boron tribromide (1.2 equiv) solution in DCM was added drop-wise. The reaction was slowly warmed up to room temperature, and stirred for 1-24 hours. To this solution was added drop-wise methanol at 0° C., then warmed to room temperature. The solution was washed with saturated NaHCO$_3$ aqueous solution, and the aqueous layer was extracted with DCM three times. The organic layer was combined and washed with brine, dried over MgSO$_4$, filtered and concentrated in vacuo.

General Procedure C: Reduction of Nitro Moiety into Primary Amine.

To a tetrahydrofuran (THF) solution of compound 5 (1.0 equiv) was added aqueous solution of sodium dithionite (3.8 equiv) at room temperature, then the solution was heated to 50° C., and stirred 1-24 hours. Aqueous 1 M HCl solution was added and then the solution was neutralized by saturated NaHCO$_3$ aqueous solution. The organic layer was separated, and the aqueous layer was extracted with ethyl acetate. The organic layer was combined and washed with brine, dried over MgSO$_4$, filtered and concentrated in vacuo.

General Procedure D: Amide Bond Formation.

To an ice-cold methyl tert-butyl ether (MTBE) solution of aniline 6 (1.0 equiv) was added saturated NaHCO$_3$ or 1 M NaOH aqueous solution, followed by slowly adding the corresponding acid chloride (1.1 equiv). This solution was stirred at room temperature 1-24 hours, then 1 M HCl aqueous solution was added. The reaction mixture was extracted with ethyl acetate. The organic layer was combined and washed with 1 M HCl$_{aq}$ twice, saturated aqueous NaHCO$_3$ solution four times, and brine, dried over MgSO$_4$, filtered and concentrated in vacuo. The target compound was purified by column chromatography, and recrystallized from acetone/DCM/hexane.

General Procedure E: Suzuki-Miyaura Coupling.

To a DME solution of compound 7 (80 mg, 177 µmol, 1.0 equiv) were added Pd (PPh$_3$)$_4$ (10 mg, 8.6 µmol, 0.05 equiv), aqueous solution of Na$_2$CO$_3$ (400 mg in 1 mL H$_2$O), and corresponding boronic acid or boronate ester (1.2 equiv) in 1 mL ethanol. This solution was stirred at 71° C. overnight. After cooling to room temperature, ethyl acetate and 1 M HCl$_{aq}$ were added and extracted four times with ethyl acetate. The organic layer was combined and washed with brine, dried over MgSO$_4$, filtered and concentrated in vacuo. The target compound was purified by column chromatography, and recrystallized from acetone/DCM/hexane.

Cif Preparation.

Recombinant Cif-His was prepared as described herein. Stocks of purified proteins were stored at 4° C. until used.

Fluorescent-Based Cif Inhibitory Assay.

IC$_{50}$ values were determined using a sensitive fluorescent-based assay similar to the method described herein and for other epoxide hydrolases (Morisseau, et al. (2011) *Analytical Biochemistry* 414(1):154-162; Jones, et al. (2005) *Analytical Biochemistry* 343(1):66-75). Cyano (6-methoxynaphthalen-2-yl) methyl glycidyl carbonate (CMNGC) was used as a fluorescent reporter substrate. Recombinant Cif (0.6 µM) was incubated with inhibitors for 5 minutes in NaPO$_4$ buffer (20 mM pH 7.0) containing 50 mM NaCl and 0.1 mg/mL of bovine serum albumin (BSA) at 37° C. prior to substrate introduction ([S]=25 µM).

Activity was measured by determining the appearance of the 6-methoxy-2-naphthaldehyde with an excitation wavelength of 330 nm and an emission wavelength of 465 nm for 10 minutes. Reported IC$_{50}$ values are the average of triplicates with at least two data points above and at least two below the IC$_{50}$. The fluorescent-based assay as performed here has a standard error between 10% and 20%, suggesting that differences of two-fold or greater are significant.

Surface Plasmon Resonance.

The interactions between Cif and inhibitors were analyzed by surface plasmon resonance using a BIACORE T100. The running buffer in immobilization was HBS-P (pH 7.4), which contains 10 mM HEPES, 150 mM NaCl, and 0.05% (v/v) TWEEN 20 surfactant. Cif was coupled to the surface of a CM5 sensor chip using standard amine-coupling chemistry with a 7-minute injection of Cif (15 µg/mL) diluted in 10 mM sodium acetate (pH 4.5). Cif protein was immobilized at 4000-5000 RU. Remaining activated groups were blocked with a 7-minute injection of M ethanolamine HCl (pH 8.5). Binding assays were performed at 37° C. at a flow rate of 30 µL/min with a 40-second injection of inhibitors followed by washing with buffer for 40 seconds. Sodium phosphate buffer (20 mM pH 7.0) containing 50 mM NaCl and 0.05% TWEEN 20 with 4% dimethyl sulfoxide (DMSO) was used as a running buffer in the assay. The measured signals were double-referenced from reference curves generated by an uncoated flow cell and several injections of running buffer. The binding affinity ($K_D$) was calculated by steady-state analysis. Experimental data were analyzed using BIAEVALUATION 1.0 software (BIACORE).

X-ray Structure Analysis.

Cif:inhibitor co-crystals were obtained by vapor diffusion against 400 µL of reservoir solution in a 4 µL hanging drop at 291 K. A solution of 5 mg/mL Cif protein containing 200 µM inhibitor was mixed in a 1:1 ratio with reservoir solution composed of 12-16% (w/v) polyethylene glycol 8000, 125 mM CaCl$_2$, 100 mM sodium acetate (pH 5), 200 µM inhibitor, and 0.2% (v/v) DMSO. Prior to data collection, crystals were washed in cryoprotectant solution composed of 12-16% (w/v) polyethylene glycol 8000, 125 mM CaCl$_2$, 100 mM sodium acetate (pH 5), 200 µM inhibitor, 0.2% (v/v) DMSO, and 20% (w/v) glycerol and flash cooled by plunging into a liquid nitrogen bath. Oscillation data were collected at 100 K at the X6A beamline of the National Synchrotron Light Source at Brookhaven National Laboratory and the 5.0.1 beamline of the Advance Light Source at Lawrence Berkeley National Laboratory. Diffraction images were processed and scaled with the XDS package (v Jan. 10, 2014; Kabsch (1993) *J. Appl. Crystall.* 26:795-800). Molecular replacement using apo-Cif-WT as the search model (PDB ID 3KD2) revealed two dimers in the asymmetric unit. Iterative rounds of automated refinement were carried out with PHENIX (v 1.7.3-928; Adams, et al. (2010) *Acta Crystallogr. D*66(2):213-221). WinCoot (v 0.7; Emsley, et al. (2004) *Acta Crystallogr. D*60(Pt 12 Pt 1):2126-32) was used for manual adjustment of the model, and PyMOL (v 1.3) was used to render structure images of the final models of chain B, in which the active-site structures are best defined. Structure figures were assembled in ADOBE ILLUSTRATOR CS6 (v16.0.4).

Thyroid Hormone Activity Assay.

Thyroid hormone activity was measured by the assay described previously with slight modifications (Freitas, et al. (2011) *Toxicology in Vitro* 25(1):257-266). GH3.TRE-Luc cells were seeded at 80% confluency in 75 cm$^2$ culture flasks (Corning, Schiphol-Rijk, Netherlands) in regular growth medium. Cells were collected and seeded into 24-well plates for an additional period of 24 hours, and incubated for 24 hours in the presence or absence of T$_3$, with the indicated test chemical in DMSO. The DMSO concentration in 500 µL of exposure medium was always the same for all exposures within an experiment and always kept ≤0.5% (v/v) to avoid cytotoxicity. Cell viability in each well was determined by measuring total protein concentration using the bicinchoninic acid (BCA) assay following the manufacturer's protocol. Luciferase activity was measured on lysed cells on an INFINITE M1000 µlate reader (Tecan Group AG, Zürich, Switzerland).

Initial SAR Around the Tiratricol Structure.

Initial structure-activity relationships (SAR) of commercially available and synthetic compounds similar to the tiratricol structure (Table 14) revealed KB2115 (1a) to be slightly more potent than tiratricol. While 1a is also a ligand selective for the thyroid hormone receptor β (Joharapurkar, et al. (2012) *J. Med. Chem.* 55(12):5649-5675; Baxter, et al. (2009) *Nature Rev. Drug Discov.* 8(4):308-320; Berkenstam, et al. (2008) *Proc. Natl. Acad. Sci. USA* 105(2):663-667), 1a does not contain any iodine atoms, in contrast to tiratricol. Given the similar potency and relative ease of analog synthesis, it was posited that 1a represents a better initial lead compound for medicinal chemistry approaches to improve its potency against Cif.

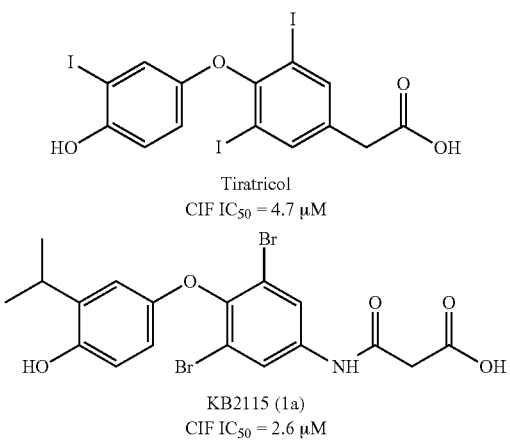

Tiratricol
CIF IC$_{50}$ = 4.7 µM

KB2115 (1a)
CIF IC$_{50}$ = 2.6 µM

Probing the Structural Requirements of Lead Compound 1a for Cif Inhibitory Potency.

Based on the general structure of Formula IV, the structural requirements of Cif inhibition by 1a were more rigorously explored.

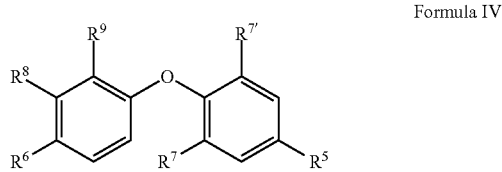

Formula IV

Compound 1a analogs were synthesized using methods similar to the one previously described for thyroid hormone analogs (WO 03/039456) as shown in Scheme 1.

SCHEME 1

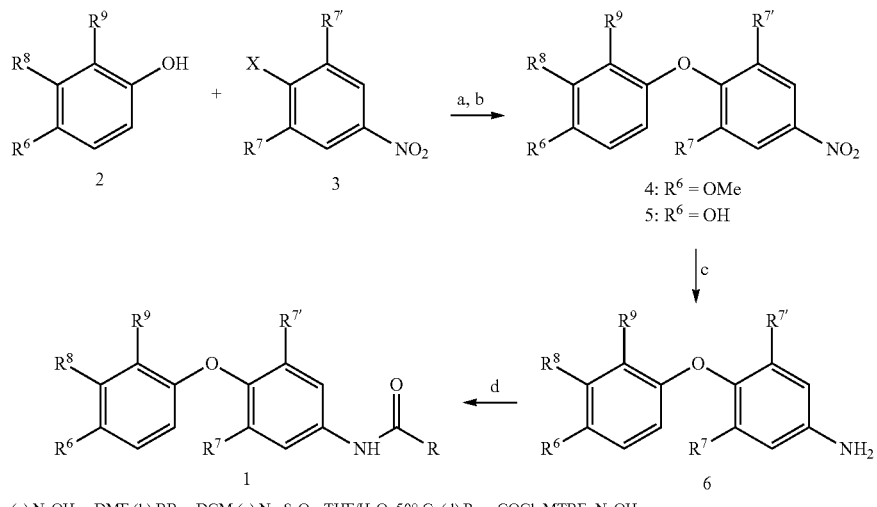

(a) NaOH$_{aq}$, DMF (b) BBr$_3$, DCM (c) Na$_2$S$_2$O$_4$, THF/H$_2$O, 50° C. (d) R—COCl, MTBE, NaOH$_{aq}$.

Briefly, an S$_N$Ar reaction between a phenol 2 and compound 3 gave a diphenyl ether 4. De-protection of a methoxy moiety by boron tribromide yielded a phenol 5. The nitro group was then reduced into a primary amine 6 using sodium dithionite. Finally, an amide bond was formed by reacting the aniline 6 with acid chloride.

The SAR of the R$^5$ functional group was studied first (Table 16). A compound with a primary amine (6a) still possessed inhibitory activity, although potency dropped approximately three-fold. Inhibitory activity was also modestly affected when the primary amine was replaced by an alkyl amide (1b, 1c). The ethyl ester form of the lead compound (1d) was also slightly less potent than the free acid form (1a). Compounds with an additional methylene moiety (1e) were as potent as 1a, with the ethyl ester form (1f) having slightly lower inhibitory activity than the free acid form.

TABLE 16

| Compound No. | R$^5$ | IC$_{50}$$^a$ (μM) |
|---|---|---|
| 1a (KB2115) | —NH—C(O)—CH$_2$—C(O)OH | 2.6 |
| 6a | —NH$_2$ | 9.7 |
| 1b | —NH—C(O)—CH$_3$ | 8.8 |
| 1c | —NH—C(O)—CH$_2$CH$_3$ | 7.5 |
| 1d | —NH—C(O)—CH$_2$—C(O)—O—CH$_2$CH$_3$ | 6.7 |
| 5a | —NO$_2$ | 10.3 |
| 1e | —NH—C(O)—CH$_2$CH$_2$—C(O)OH | 3.2 |
| 1f | —NH—C(O)—CH$_2$CH$_2$—C(O)—O—CH$_2$CH$_3$ | 5.5 |

$^a$IC$_{50}$ values were determined with a fluorescent-based assay using CMNGC as a fluorescent reporter substrate (see methods section). Reported IC$_{50}$ values are the average of triplicates with at least two data points above and at least two below the IC$_{50}$. The fluorescent-based assay as performed here has a standard error between 10% and 20%, suggesting that differences of two-fold or greater are significant.

These data indicate that the terminal free carboxylic moiety interacts only weakly with the enzyme. In further synthesis of analogs for this initial SAR study, there were difficulties in purifying some of the analogs with free acid forms on R$^5$. Therefore, for the purpose of determining structural requirements at other positions, the malonate ethyl ester moiety was selected as the $R^5$ moiety for further SAR study.

Results for the structural requirements of the $R^6$, $R^7$, $R^8$ and $R^9$ functional groups are shown in Table 17. When the hydroxyl moiety at $R^6$ is replaced either by hydrogen (1g) or methoxide (1h), these analogs fail to show inhibitory activity at 50 μM, indicating that the hydroxyl moiety is critical for inhibitory activity and that a hydrogen bonding acceptor is not sufficient for the interaction. Replacement of bromides on $R^7$ and $R^{7'}$ with chlorides (1i) results in an approximately two-fold increase in activity. Removal of one of the chlorides (1j) leads to a decrease in activity, reflecting the importance of the halide $R^7$ substituents.

TABLE 17

| Compound | $R^6$ | $R^7$ | $R^8$ | $R^9$ | $IC_{50}^a$ (μM) |
|---|---|---|---|---|---|
| 1d | OH | $R^7 = R^{7'} = Br$ | Isopropyl | H | 6.7 |
| 1g | H | $R^7 = R^{7'} = Br$ | Isopropyl | H | >50 |
| 1h | OCH$_3$ | $R^7 = R^{7'} = Br$ | Isopropyl | H | >50 |
| 1i | OH | $R^7 = R^{7'} = Cl$ | Isopropyl | H | 3.8 |
| 1j | OH | $R^7 = Cl, R^{7'} = H$ | Isopropyl | H | 11.6 |
| 1k | OH | $R^7 = R^{7'} = Cl$ | H | H | >50 |
| 1l | OH | $R^7 = R^{7'} = Cl$ | Br | H | 4.9 |
| 1m | OH | $R^7 = R^{7'} = Cl$ | I | H | 3.8 |
| 1n | OH | $R^7 = R^{7'} = Cl$ | CF$_3$ | H | 3.0 |
| 1p | OH | $R^7 = R^{7'} = Cl$ | Ethynyl | H | 2.9 |
| 1q | OH | $R^7 = R^{7'} = Cl$ | H | Br | 29.3 |

$^a$IC$_{50}$ values were determined with a fluorescent-based assay using CMNGC as a fluorescent reporter substrate (see methods section). Reported IC$_{50}$ values are the average of triplicates with at least two data points above and at least two below the IC$_{50}$. The fluorescent-based assay as performed here has a standard error between 10% and 20%, suggesting that differences of two-fold or greater are significant.

The SAR of $R^8$ and $R^9$ were also analyzed. Replacement of the $R^8$ isopropyl with a proton yielded the non-substituted compound (1k), which showed no inhibition at 50 μM, indicating that the substituent at $R^8$ is important for the potency. Replacement of the isopropyl moiety with bromide (1l), iodide (1m), trifluoromethyl (1n), or acetylene (1p) moieties does not change the potency of the compound. This indicates the existence of available space in the binding pocket of Cif that can be filled by an $R^8$ substituent of the appropriate steric volume, but that its exact chemistry is not precisely constrained. A compound with bromide at the $R^9$ position (1q) has much lower potency than the corresponding $R^9$ substituent (1l), but slightly greater potency than the unsubstituted compound (1k) reflecting greater selectivity at the $R^9$ position.

Replacing the $R^9$ isopropyl moiety with a trifluoromethyl moiety (1n), which is a strong electron withdrawing group, increases the acidity of the phenol on $R^6$. Thus, it was expected that compound 1n would form stronger hydrogen bonds with the enzyme amino acids, leading to higher inhibitory potency. However, compared to 1i, the potency of 1n did not improve dramatically.

Cif:1a Structure.

In parallel with the SAR studies, the X-ray crystallographic structure of Cif complexed with lead compound 1a was determined at a resolution of 1.65 Å. The resulting model revealed that 1a occludes access to the catalytic pocket. Globally, the structure confirmed the findings from the medicinal chemistry approach. For example, the structure showed that the $R^5$ moiety is located outside of the active-site tunnel and is not critical for the interaction with Cif, consistent with the SAR data showing that changes of the $R^5$ chain had little effect on Cif inhibition potency (Table 16). The structure also showed that the hydroxyl moiety at the $R^6$ position forms a hydrogen bond with the main-chain carbonyl oxygen of Gly270. This confirmed the observation that removing this hydroxyl moiety results in great loss of potency (Table 17). One of the bromides ($R^7$) is close to the hydroxyl of Ser173 and the main-chain amide nitrogens of Leu174 and Val175, while the other bromide ($R^{7'}$) is close to the thioether of Met272, indicating potential interactions between the halogens and these residues (Wilcken, et al. (2013) J. Med. Chem. 56(4):1363-1388). In addition, dibromophenyl ring of compound 1a appears to form a π-stacking interaction with Phe164, which may be strengthened by halogen substituents (Sinnokrot, et al. (2004) J. Am. Chem. Soc. 126:7690-7; Bissantz, et al. (2010) J. Med. Chem. 53:5061-84). The catalytic cavity opens around the isopropyl moiety of 1a, indicating that larger groups could be present at position $R^8$, as observed with the medicinal chemistry approach (Table 17).

The structural requirements of Cif inhibitors overlap with those of thyroid hormone receptor ligands (Joharapurkar, et al. (2012) J. Med. Chem. 55(12):5649-5675) at several positions. Tiratricol and 1a reflect the intersection of these requirements, and thus serve as both thyroid hormone mimics and Cif inhibitors. For example, the hydroxyl group on $R^6$ and two halogens on $R^7$ and $R^{7'}$ are required in both cases, and a bulky substituent is preferred on $R^8$. In the case of the thyroid hormone receptor, the terminal free acid of $R^5$ forms hydrogen bonds. On the other hand, the terminal free acid is not required for Cif inhibition (Table 16). Therefore, compounds with different $R^5$ groups were screened to evaluate their thyroid hormone activity. The compound with propyl amide (1c) showed the lowest thyroid hormone activity while still effectively inhibiting Cif. Therefore, the propyl amide moiety was selected as the $R^5$ moiety for further structural optimization.

Comparison to Mammalian EH and their Inhibitors, and Inhibitor Design Strategy.

In the case of mammalian epoxide hydrolases, urea and amide moieties are known to function as transition state analogs (Decker, et al. (2012) J. Lipid Res. 53:2038-45; Arand, et al. (1996) J. Biol. Chem. 271:4223-9; Gomez, et al. (2006) Prot. Sci. 15:58-64). These moieties bind to the catalytic site very tightly by interacting non-covalently with the catalytic nucleophile Asp and the accessory Tyr-Tyr pair, leading to potent inhibition of these enzymes (Arand, et al. (1996) J. Biol. Chem. 271:4223-9; Gomez, et al. (2006) Prot. Sci. 15:58-64; Amano, et al. (2014) Bioorgan. Med. Chem. 22:2427-34; Morisseau, et al. (1999) Proc. Natl. Acad. Sci. USA 96:8849-54; Morisseau, et al. (2008) Chem. Res. Toxicol. 21:954-7; Morisseau, et al. (2001) Chem. Res. Toxicol. 14:409-15). Cif has a conserved EH catalytic triad composed of residues Asp129, Glu153 and His297, while it uses an alternative His177-Tyr239 accessory pair to coordinate the epoxide oxygen during ring opening (Bahl (2012) Protein Pept. Lett. 19:186-93). Based on the similar active-site chemistries, it was expected that urea or amide functionalities could also interact with the catalytic site of Cif. However, simple alkyl urea/amide/carbamate compounds failed to show Cif inhibitory activity at 50 μM, as did a series of additional potent mammalian EH inhibitors with urea or amide pharmacophores (Table 15). The differential sensitivity of the mammalian and bacterial EHs is consistent with the discovery that these enzymes differ in the relative kinetics of formation vs. hydrolysis of a covalent intermediate, and indicates that the fine details of the transition states of the two EH families are distinct.

In the Cif:1a complex structure, an acetate ion was found in the catalytic site of the enzyme, which was crystallized in a buffer containing sodium acetate. The active-site hydrogen bonding network included interactions between the acetate ion and the catalytic site residues Asp129, His177 and Tyr239, replicating many of the interactions of the local water network observed in the apo structure. The distance between the isopropyl moiety and the acetate was roughly 4.5 Å. The theoretical distance between the carbonyl and phenyl ring in compounds that have a phenyl carbonyl moiety at the $R^8$ position was approximately 4.3 Å, indicating that a phenyl linker may have the appropriate length to reach the catalytic site.

Improving Potency by Targeting the Catalytic Site.

Based on the above results, the lead compound was connected to a moiety that interacts directly with catalytic residues with the aim to improve the inhibitory potency on Cif by creating an additional interaction between the inhibitor and the enzyme. A series of compounds were designed to target the catalytic site by extending the $R^8$ position. As shown in Scheme 2, these compounds were synthesized by Suzuki-Miyaura cross coupling between an iododiphenyl ether and various substituted phenylboronic acids or esters, using $Pd(PPh_3)_4$ as a palladium catalyst and sodium carbonate as a base (Miyaura & Suzuki (1995) Chem. Rev. 95:2457-83).

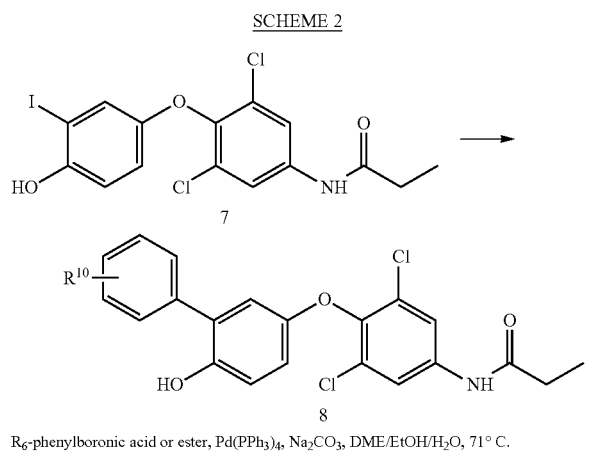

SCHEME 2

$R_6$-phenylboronic acid or ester, $Pd(PPh_3)_4$, $Na_2CO_3$, DME/EtOH/$H_2O$, 71° C.

The potencies of the resulting compounds as Cif inhibitors are shown in Table 18.

TABLE 18

| Compound No. | R | $IC_{50}^a$ (μM) |
|---|---|---|
| 8a | H | 1.4 |
| 8b | p-COOH | 10.5 |
| 8c | p-CONH$_2$ | 0.35 |
| 8d | m-CONH$_2$ | 0.46 |
| 8e | p-CN | 11.9 |
| 8f | m-CN | 0.58 |
| 8g | p-CONHMe | 1.7 |

TABLE 18-continued

| Compound No. | R | $IC_{50}^a$ (μM) |
|---|---|---|
| 8i | p- H$_2$N–C(=O)–NH– | 0.29 |
| 8j | p- CH$_3$–C(=O)–NH– | 15.6 |
| 8k | p- CH$_3$–C(=O)– | 0.35 |
| 8l | p- H$_2$N–S(=O)$_2$– | 2.0 |

$^a$IC$_{50}$ values were determined with a fluorescent-based assay using CMNGC as a fluorescent reporter substrate (see methods section). Reported IC$_{50}$ values are the average of triplicates with at least two data points above and at least two below the IC$_{50}$. The fluorescent-based assay as performed here has a standard error between 10% and 20%, suggesting that differences of two-fold or greater are significant.

A compound with para carboxylic acid (8b) showed a significant loss of activity, while compounds with para amide (8c), urea (8h), or acetyl (8j) showed potencies almost 10-fold higher than that of the lead compound, reaching the limit of quantification of the fluorescent-based Cif inhibition assay ([E]=0.6 μM in the assay). For more classical epoxide hydrolases, ureas and amides are pharmacophores for potent inhibitors that establish bonds with catalytic residues, but ketones are not (Morisseau, et al. (1999) Proc. Natl. Acad. Sci. USA 96:8849-54), underscoring the distinct chemistry of the Cif active site. In the case of free amides, both para (8c) and meta (8d) substituents yielded high potencies, with the para substituent slightly favored. In the case of nitrile, the meta substituent (8f) showed higher potency but the para substituent (8e) showed significant decrease in potency. Compounds with a methyl amide (8g) or a sulfonamide substituent (8k) also showed significantly lower potency than corresponding free amide.

Surface Plasmon Resonance (SPR).

To confirm potency, particularly for the highest-affinity compounds, binding interactions between Cif and inhibitors were further examined by SPR. Results are presented in Table 19.

TABLE 19

| Compound | $K_D^a$ (μM) |
|---|---|
| Tiratricol | 115 ± 11 |
| 1a (KB2115) | 113 ± 24 |
| 8c | 2.0 ± 0.6 |
| 8h | 3.3 ± 0.4 |
| 8j | 4.4 ± 0.5 |

Results are shown as mean ± SD (n = 3 – 6).
$^a$Data calculated based on steady state analysis.

Compound 1a and tiratricol showed similar affinity ($K_D$), and compounds 8c, 8h and 8j showed 30- to 50-fold higher affinity than lead compound 1a, compared to a 7-fold difference in IC$_{50}$. Overall, the affinity values from the SPR experiments were approximately 10- to 40-fold weaker than the $IC_H$ values obtained from the enzyme activity-based assay. This could be due to conformational change of Cif by immobilization on the chip surface, cooperative effects, or differences in experimental conditions, such as the presence of surfactant and DMSO concentration in the running buffer.

Structures of Second-Generation Cif Inhibitors.

X-ray crystallographic analysis was performed in order to further characterize the interaction between the new inhibitors and the Cif protein. This analysis indicated that the amide or urea moieties in compounds 8c and 8h interact with catalytic residues: the nucleophile Asp129, and Tyr239 and His177, which coordinate the epoxide substrate. The NH group of amide and urea forms hydrogen bonds with Asp129, while the oxygen in the carbonyl hydrogen bond to His177 and Try239. As with the acetate in the Cif:1a structure, the binding of 8c and 8h occupies the volume and thus replaces the tetrahedral water network found in the apo crystal structure. By shifting the specific hydrogen-bonding network in the active site, 8c and 8h promote a hydrogen bond between His297 and Asp129. This new bond displaces the hydrogen bond with the catalytic water that is activated by the His297/Glu153 pair under hydrolysis conditions.

The structures also provide a framework to interpret the SAR relationships revealed by the compound series (Tables 18 and 19). It appears that the meta substituents (8d and 8f) can each be accommodated at the edge of the catalytic core. Interestingly, among the para substituents either an amide (8c), a urea (8h) or a ketone (8j) moiety causes a substantial increase in potency against Cif. Although chemically distinct, each of these groups can be sterically accommodated between the catalytic aspartic acid and the ring-opening pair, forming hydrogen bonds that lie roughly within the plane of view analyzed. In contrast, weaker binding affinities are observed for para substituents with charge incompatibility (8b), out-of-plane hydrogen-bond orientations (8k), or a combination of steric and hydrogen-bonding incompatibility (8e, 8g, 8i).

Selectivity Profile and In Vitro Metabolic Stability of Selected Compounds.

Three inhibitors, 8c, 8h and 8j, were selected based on their Cif inhibitory potency (Table 18). Thyroid receptor induction activity (relative to 10 nM $T_3$) was measured at a concentration of 10 μM. Results show that compounds 8c, 8h and 8j lost their thyroid hormone agonistic activity ($EC_{50}$>10 μM), while they displayed a weak antagonistic activity (Table 20).

TABLE 20

| Activity | Compound | | | |
|---|---|---|---|---|
| | 1a (KB2115) | 8c | 8h | 8j |
| TR agonist $EC_{50}$ (nM) | 0.43 ± 0.14 | >10,000 | >10,000 | >10,000 |
| TR antagonist (% inhibition at 10 (μM) | — | 66% | 28% | 33% |
| Human sEH $IC_{50}$ (μM) [a] | — | 8.6 | 7.5 | 7.7 |
| Human mEH $IC_{50}$ (μM) [b] | — | 17.2 | 26.3 | 97.8 |
| Human liver microsomal stability $t_{1/2}$ (min) | — | 15 | 29 | 5.7 |

TABLE 20-continued

| Activity | Compound | | | |
|---|---|---|---|---|
| | 1a (KB2115) | 8c | 8h | 8j |
| Stability in cell culture (%) [c] | — | 106 ± 8 | 103 ± 12 | 74 ± 30 |
| Molecular weight | 487 | 445 | 460 | 444 |
| Melting point (° C.) | — | 264-265 | 162.0-162.9 | 190-194 |
| LogP [d] | 4.71 | 4.44 | 4.11 | 4.85 |
| Solubility (μM) [e] | — | 0.17 | 21 | <0.04 |

[a] Measured using t-DPPO ([³H] trans-diphenylpropene oxide) as a substrate;
[b] Measured using c-SO ([³H] cis-stilbene oxide) as a substrate.
[c] Percentage remaining after 24 h incubation (initial conc: 10 μM) with GH3.TRE-Luc cell (mean ± SD) are shown.
[d] Predicted value using Chembiodraw Ultra 13.0.
[e] Solubility in sodium phosphate buffer (0.1M, pH 7.4).

Globally, compared to 1a, the novel Cif inhibitors are more than 150,000-fold more selective for Cif than for the thyroid hormone receptor. Inhibition of human soluble epoxide hydrolase (sEH) and microsomal epoxide hydrolase (mEH) was also measured. The $IC_{50}$ values obtained 8 μM for sEH, and 20-100 μM for mEH) are 100-10,000 fold higher than the best inhibitors for these enzymes (Morisseau, et al. (1999) Proc. Natl. Acad. Sci. USA 96:8849-54), indicating that 8c, 8h and 8j are poor inhibitors for the mammalian EHs. Given the potency of these compounds against Cif, they have at least a 27-fold selectivity toward Cif over sEH and at least a 50-fold selectivity toward Cif over mEH.

Metabolic stability of the three selected compounds was then studied in both liver microsomes and cell cultures (Kim, et al. (2012) *Bioorgan. Med. Chem. Lett.* 22:5889-92). Results (Table 20) indicate that compound 8h is the most stable of the trio, followed in order by 8c and 8j. Compound 8a, which does not have a substituent on the biphenyl ring (Table 18), has a half-life longer than 60 minutes in the liver microsomal stability assay (63% remained after 60 min incubation). This value is more than double the corresponding value for 8h, indicating that the substituent on the biphenyl ring is the most susceptible to metabolism.

The physico-chemical properties of the selected compounds were also determined. While the three compounds have similar molecular weight, compound 8h has a lower melting point. In addition, this compound has a lower predicted Log P and much higher aqueous solubility without DMSO as a co-solvent than 8c and 8j, indicating that 8h may be easier to formulate, and is likely more bioavailable. None of the three compounds triggered significant protein release from GH3.TRE-Luc when applied at a concentrated of 10 μM. In addition, neither 8c nor 8h showed cytotoxicity when applied to polarized monolayers of airway epithelial cells at concentrations up to 10 μM. Overall, in terms of potency, selectivity, metabolic stability, solubility and toxicity, compound 8h is expected to be an efficacious Cif inhibitor against *Pseudomonas* infection.

What is claimed is:

1. A pharmaceutical composition formulated for pulmonary administration comprising an inhibitor of Cystic fibrosis transmembrane conductance regulator Inhibitory Factor (Cif) activity in admixture with a pharmaceutically acceptable carrier, wherein the inhibitor of Cif activity has the structure of Formula I

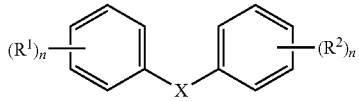

Formula I wherein
X is absent or present and when present is —O—, —NH—, —S—, —CH$_2$—, —NHC(O)NH—, or —C(O)NHC(O)NH—;
n is 1 to 5;
m is 2 to 5; and
R$^1$ and R$^2$ are substituted anywhere on their respective rings, wherein
each occurrence of R$^1$ is independently a hydrogen, hydroxyl, amino, cyano, halo, nitro, mercapto, phosphate, —SO$_2$NH$_2$, —CH(CH$_3$)$_2$, —COOH, —C(O)CH$_3$, —CO$_2$Me, —CONHNH$_2$, —CONHCH$_3$, —NHC(O)R$^{11}$, —OCH$_2$COOH, —OC(O)CH$_2$CH$_3$, alkyl, alkenyl, alkynyl, aryl, alkoxy, or amido group;
at least one R$^2$ is a nitro, or —NHC(O)R$^{11}$ group; at least one R$^2$ is halo; and each other occurrence of R$^2$ is independently a hydrogen, hydroxyl, amino, cyano, halo, nitro, mercapto, phosphate, —SO$_2$NH$_2$, —CH(CH$_3$)$_2$, —COOH, —C(O)CH$_3$, —CO$_2$Me, —CONHNH$_2$, —CONHCH$_3$, —NHC(O)R$^{11}$, —OCH$_2$COOH, —OC(O)CH$_2$CH$_3$, alkyl, alkenyl, alkynyl, aryl, alkoxy, or amido group,
wherein R$^{11}$ is an alkyl, amino, —CH$_2$C(O)OCH$_2$CH$_3$, —CH$_2$CH$_2$COOH, —CH$_2$CH$_2$C(O)OCH$_2$CH$_3$, —CH(CH$_3$)$_2$ group.

2. A method for ameliorating or treating a respiratory disease, or a secondary infection thereof, comprising administering to a subject in need of treatment the pharmaceutical composition of claim 1, thereby ameliorating or treating the subject's respiratory disease, or secondary infection thereof.

3. The method of claim 2, wherein the respiratory disease is chronic obstructive pulmonary disease, pneumonia, a *Pseudomonas aeruginosa* infection, an *Acinetobacter* infection or cystic fibrosis.

4. The method of claim 2, wherein the secondary infection is a viral infection, an *Acinetobacter* infection or a *Pseudomonas aeruginosa* infection.

5. A pharmaceutical composition formulated for pulmonary administration comprising an inhibitor of Cystic fibrosis transmembrane conductance regulator Inhibitory Factor (Cif) activity in admixture with a pharmaceutically acceptable carrier, wherein the inhibitor of Cif activity has the structure of Formula IV,

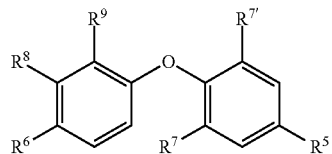

Formula IV wherein
$R^5$ is amino, nitro, or —NHC(O)$R^{11}$ group;
$R^6$ is a hydroxyl group;
$R^7$ and $R^{7'}$ are independently a hydrogen or halo group;
$R^8$ is an hydroxyl, amino, cyano, halo, nitro, mercapto, phosphate, —SO$_2$NH$_2$, —COOH, —C(O)CH$_3$, —CO$_2$Me, —CONHNH$_2$, —CONHCH$_3$, —NHC(O)$R^{11}$, —OCH$_2$COOH, —OC(O)CH$_2$CH$_3$, alkyl, alkenyl, alkynyl, aryl, alkoxy, or amido group;
$R^9$ is a hydrogen group; and
$R^{11}$ is
  (i) alkyl,
  (ii) amino,
  (iii) —(CH$_2$)$_x$C(O)OCH$_2$CH$_3$, wherein x is 1 to 5, or
  (iv) —(CH$_2$)$_x$COOH, wherein x is 2 to 5.

* * * * *